United States Patent
Butler et al.

(10) Patent No.: US 9,241,971 B1
(45) Date of Patent: Jan. 26, 2016

(54) TOPICAL VANCOMYCIN FORMULATION AND METHODS OF USE

(71) Applicant: Kurobe Pharmaceuticals, Inc., Tampa Bay, FL (US)

(72) Inventors: Barry Butler, Tarpon Springs, FL (US); William Stringer, St. Petersburg, IL (US); Colin Butler, Murfreesboro, TN (US); Jeremy Brace, Seminole, FL (US); Ronil Patel, Temple Terrace, FL (US)

(73) Assignee: KUROBE, LLC, Tampa Bay, FL (US)

( * ) Notice: Subject to any disclaimer, the term of this patent is extended or adjusted under 35 U.S.C. 154(b) by 0 days.

(21) Appl. No.: 14/495,669

(22) Filed: Sep. 24, 2014

Related U.S. Application Data

(60) Provisional application No. 62/026,534, filed on Jul. 18, 2014.

(51) Int. Cl.
| | | |
|---|---|---|
| *A61K 9/26* | (2006.01) | |
| *A61K 38/14* | (2006.01) | |
| *A61K 9/10* | (2006.01) | |
| *A61K 9/06* | (2006.01) | |
| *A61K 9/00* | (2006.01) | |
| *C12Q 1/04* | (2006.01) | |

(52) U.S. Cl.
CPC .............. *A61K 38/14* (2013.01); *A61K 9/0014* (2013.01); *A61K 9/06* (2013.01); *A61K 9/10* (2013.01); *C12Q 1/04* (2013.01)

(58) Field of Classification Search
None
See application file for complete search history.

(56) References Cited

U.S. PATENT DOCUMENTS

| | | | |
|---|---|---|---|
| 4,421,741 A | 12/1983 | Gilbert et al. | |
| 4,507,287 A | 3/1985 | Dixon | |
| 6,461,624 B2 | 10/2002 | Eggers et al. | |
| 6,551,584 B2 | 4/2003 | Bandyopadhyay et al. | |
| 6,852,311 B1 | 2/2005 | Kasama et al. | |
| 7,144,857 B2 | 12/2006 | Dharan et al. | |
| 7,923,021 B2 | 4/2011 | Haggard et al. | |
| 8,426,466 B2 | 4/2013 | Shih | |
| 8,481,280 B1 * | 7/2013 | Haas | 435/32 |
| 2002/0048592 A1 | 4/2002 | Eggers et al. | |
| 2002/0107238 A1 | 8/2002 | Bandyopadhyay et al. | |
| 2004/0266702 A1 | 12/2004 | Dawson et al. | |
| 2005/0159342 A1 | 7/2005 | Dharan et al. | |
| 2005/0244522 A1 | 11/2005 | Carrara et al. | |
| 2008/0124400 A1 * | 5/2008 | Liggins et al. | 424/501 |
| 2010/0267624 A1 | 10/2010 | De Tommaso | |
| 2011/0165114 A1 | 7/2011 | McCoy et al. | |
| 2011/0206620 A1 | 8/2011 | Dana et al. | |
| 2012/0128622 A1 * | 5/2012 | Berman | 424/78.06 |
| 2013/0045927 A1 | 2/2013 | Dana et al. | |
| 2013/0108670 A1 | 5/2013 | Lynch et al. | |
| 2013/0108683 A1 | 5/2013 | Lynch et al. | |
| 2013/0171224 A1 | 7/2013 | Percival et al. | |

FOREIGN PATENT DOCUMENTS

| | | | |
|---|---|---|---|
| EP | 1210947 | * | 6/2000 |
| WO | WO85/00108 | | 1/1985 |
| WO | WO98/58627 | | 12/1998 |
| WO | WO02/04012 | | 1/2002 |
| WO | WO2009/056547 | | 5/2009 |
| WO | WO2011/089379 | | 7/2011 |
| WO | WO2011/103788 | | 9/2011 |
| WO | WO2011/106697 | | 9/2011 |
| WO | WO2013/062994 | | 5/2013 |
| WO | WO2013/062995 | | 5/2013 |

OTHER PUBLICATIONS

Ikeda et al. Vancomycin Ointment for MRSA Infection at a Cranioplasty Site. Ann Pharmacother 38(1):70-72 (2004).
PCT/US2015/041025 International Search Report and Written Opinion dated Oct. 29, 2015.

* cited by examiner

*Primary Examiner* — Scott Long
*Assistant Examiner* — Sarah Alawadi
(74) *Attorney, Agent, or Firm* — Wilson Sonsini Goodrich & Rosati

(57) ABSTRACT

Disclosed herein are methods, compositions, and kits for treating a skin condition caused by a bacterial infection at a skin depth with a topical ointment comprising vancomycin hydrochloride. Also disclosed herein are methods, compositions, and kits for testing susceptibility of vancomycin for treating a bacterial infection at a skin depth, and of optimizing a topical ointment therapeutic regimen.

14 Claims, 7 Drawing Sheets

Fig. 3

| Tissue | Treatment | Timepoint (hr) | Animal ID | Calculated Concentration (ng/mL) |
|---|---|---|---|---|
| Plasma | a. Undosed | 0 | 101 | <50 |
| Plasma | a. Undosed | 0 | 102 | <50 |
| Plasma | b. Low Topical Dose, Non-abraded Skin | 1 | 205 | <50 |
| Plasma | b. Low Topical Dose, Non-abraded Skin | 1 | 206 | <50 |
| Plasma | b. Low Topical Dose, Non-abraded Skin | 2 | 203 | <50 |
| Plasma | b. Low Topical Dose, Non-abraded Skin | 2 | 204 | <50 |
| Plasma | b. Low Topical Dose, Non-abraded Skin | 4 | 201 | <50 |
| Plasma | b. Low Topical Dose, Non-abraded Skin | 4 | 202 | <50 |
| Plasma | b. Low Topical Dose, Non-abraded Skin | 24 | 207 | <50 |
| Plasma | b. Low Topical Dose, Non-abraded Skin | 24 | 208 | <50 |
| Plasma | c. High Topical Dose, Non-abraded Skin | 1 | 305 | <50 |
| Plasma | c. High Topical Dose, Non-abraded Skin | 1 | 306 | <50 |
| Plasma | c. High Topical Dose, Non-abraded Skin | 2 | 303 | <50 |
| Plasma | c. High Topical Dose, Non-abraded Skin | 2 | 304 | <50 |
| Plasma | c. High Topical Dose, Non-abraded Skin | 4 | 301 | <50 |
| Plasma | c. High Topical Dose, Non-abraded Skin | 4 | 302 | <50 |
| Plasma | c. High Topical Dose, Non-abraded Skin | 24 | 307 | <50 |
| Plasma | c. High Topical Dose, Non-abraded Skin | 24 | 308 | <50 |
| Plasma | d. Low Topical Dose, Abraded Skin | 1 | 405 | <50 |
| Plasma | d. Low Topical Dose, Abraded Skin | 1 | 406 | <50 |
| Plasma | d. Low Topical Dose, Abraded Skin | 2 | 403 | <50 |
| Plasma | d. Low Topical Dose, Abraded Skin | 2 | 404 | <50 |
| Plasma | d. Low Topical Dose, Abraded Skin | 4 | 401 | <50 |
| Plasma | d. Low Topical Dose, Abraded Skin | 4 | 402 | <50 |
| Plasma | d. Low Topical Dose, Abraded Skin | 24 | 407 | <50 |
| Plasma | d. Low Topical Dose, Abraded Skin | 24 | 408 | <50 |
| Plasma | e. High Topical Dose, Abraded Skin | 1 | 505 | <50 |
| Plasma | e. High Topical Dose, Abraded Skin | 1 | 506 | <50 |
| Plasma | e. High Topical Dose, Abraded Skin | 2 | 503 | <50 |
| Plasma | e. High Topical Dose, Abraded Skin | 2 | 504 | 431† |
| Plasma | e. High Topical Dose, Abraded Skin | 4 | 501 | <50 |
| Plasma | e. High Topical Dose, Abraded Skin | 4 | 502 | <50 |
| Plasma | e. High Topical Dose, Abraded Skin | 24 | 507 | <50 |
| Plasma | e. High Topical Dose, Abraded Skin | 24 | 508 | <50 |
| Plasma | f. Introvenous Dose | 1 | 605 | 14900 |
| Plasma | f. Introvenous Dose | 1 | 606 | 7430 |
| Plasma | f. Introvenous Dose | 2 | 603 | 3640 |
| Plasma | f. Introvenous Dose | 2 | 604 | 6850 |
| Plasma | f. Introvenous Dose | 4 | 601 | 145 |
| Plasma | f. Introvenous Dose | 4 | 602 | 148 |
| Plasma | f. Introvenous Dose | 24 | 607 | <50 |
| Plasma | f. Introvenous Dose | 24 | 608 | <50 |

| Tissue | Treatment | Timepoint (hr) | Animal ID | Calculated Homogenate Concentration (ng/mL) | Corrected Tissue Concentration (ng/g) | Ratio of Derm to IV | Mean ratio over all time points | Corrected Tissue Concentration ratio of derm to IV | Mean of Corrected Tissue ratios |
|---|---|---|---|---|---|---|---|---|---|
| Dermis | a. Undosed | 0 | 101 | < 15 | | | | | |
| Dermis | a. Undosed | 0 | 102 | < 15 | | | | | |
| Dermis | b. Low Topical Dose, Non-abraded Skin | 1 | 203 | 965 | 2397 | 0.15 | 0.353631161 | 0.17 | 0.835429999 |
| Dermis | b. Low Topical Dose, Non-abraded Skin | 1 | 206 | 95.3 | 264 | 0.06 | | 0.08 | |
| Dermis | b. Low Topical Dose, Non-abraded Skin | 2 | 203 | 198 | 547 | 0.05 | | 0.08 | |
| Dermis | b. Low Topical Dose, Non-abraded Skin | 2 | 204 | 63.3 | 180 | 0.66 | | 0.74 | |
| Dermis | b. Low Topical Dose, Non-abraded Skin | 4 | 201 | 723 | 2232 | 1.32 | | 1.49 | |
| Dermis | b. Low Topical Dose, Non-abraded Skin | 4 | 202 | 35.2 | 99 | | | | |
| Dermis | b. Low Topical Dose, Non-abraded Skin | 24 | 207 | 54.5 | 193 | | | | |
| Dermis | b. Low Topical Dose, Non-abraded Skin | 24 | 208 | 24.4 | 68 | | | | |
| Dermis | c. High Topical Dose, Non-abraded Skin | 1 | 305 | 863 | 2371 | 0.11 | 2.803241651 | 0.18 | 2.948036446 |
| Dermis | c. High Topical Dose, Non-abraded Skin | 1 | 306 | 65.2 | 199 | | | | |
| Dermis | c. High Topical Dose, Non-abraded Skin | 2 | 303 | 12700 | 31026 | 3.28 | | 3.13 | |
| Dermis | c. High Topical Dose, Non-abraded Skin | 2 | 304 | 708 | 1863 | | | | |
| Dermis | c. High Topical Dose, Non-abraded Skin | 4 | 301 | 1640 | 4091 | 1.63 | | 1.59 | |
| Dermis | c. High Topical Dose, Non-abraded Skin | 4 | 302 | 282 | 517 | | | | |
| Dermis | c. High Topical Dose, Non-abraded Skin | 24 | 307 | 273 | 3855 | 6.65 | | 7.03 | |
| Dermis | c. High Topical Dose, Non-abraded Skin | 24 | 308 | 91.5 | 320 | | | | |
| Dermis | d. Low Topical Dose, Abraded Skin | 1 | 405 | 1590 | 4379 | 0.24 | 0.398426565 | 0.30 | 0.955948342 |
| Dermis | d. Low Topical Dose, Abraded Skin | 1 | 406 | 95.8 | 205 | | | | |
| Dermis | d. Low Topical Dose, Abraded Skin | 2 | 403 | 396 | 1082 | 0.22 | | 0.17 | |
| Dermis | d. Low Topical Dose, Abraded Skin | 2 | 404 | 72.6 | 230 | | | | |
| Dermis | d. Low Topical Dose, Abraded Skin | 4 | 401 | 332 | 1137 | 0.31 | | 0.40 | |
| Dermis | d. Low Topical Dose, Abraded Skin | 4 | 402 | 14.5 | 54 | | | | |
| Dermis | d. Low Topical Dose, Abraded Skin | 24 | 407 | 103 | 318 | 1.73 | | 1.82 | |
| Dermis | d. Low Topical Dose, Abraded Skin | 24 | 408 | 7.15 | | | | | |
| Dermis | e. High Topical Dose, Abraded Skin | 1 | 505 | 7900 | 23984 | 1.1 | 3.004578753 | 1.69 | 6.237912273 |
| Dermis | e. High Topical Dose, Abraded Skin | 1 | 506 | 332 | 985 | | | | |
| Dermis | e. High Topical Dose, Abraded Skin | 2 | 503 | 9890 | 22700 | 2.49 | | 2.33 | |
| Dermis | e. High Topical Dose, Abraded Skin | 2 | 504 | 651 | 1787 | | | | |
| Dermis | e. High Topical Dose, Abraded Skin | 4 | 501 | 3440 | 9260 | 1.25 | | 2.14 | |
| Dermis | e. High Topical Dose, Abraded Skin | 4 | 502 | 567 | 1634 | | | | |
| Dermis | e. High Topical Dose, Abraded Skin | 24 | 507 | 427 | 1308 | 7.16 | | 18.69 | |
| Dermis | e. High Topical Dose, Abraded Skin | 24 | 508 | 833 | 3938 | | | | |
| Dermis | f. Intravenous Dose | 1 | 605 | 4460 | 9839 | | | | |
| Dermis | f. Intravenous Dose | 1 | 606 | 2260 | 9564 | | | | |
| Dermis | f. Intravenous Dose | 2 | 603 | 711 | 2365 | | | | |
| Dermis | f. Intravenous Dose | 2 | 604 | 3260 | 9268 | | | | |
| Dermis | f. Intravenous Dose | 4 | 601 | 318 | 1434 | | | | |
| Dermis | f. Intravenous Dose | 4 | 602 | 735 | 2020 | | | | |
| Dermis | f. Intravenous Dose | 24 | 607 | 32.4 | 107 | | | | |
| Dermis | f. Intravenous Dose | 24 | 608 | 24.8 | 68 | | | | |

| Tissue | Treatment | Timepoint (h.) | Animal ID | Calculated Homogenate Concentration (ng/mL) | Corrected Tissue Concentration (ng/g) | Ratio of Derm Mean ratio over all to IV | time points | Weight adjusted ratio | Mean of Weight adjusted ratios |
|---|---|---|---|---|---|---|---|---|---|
| Muscle, 1 inch from Dose Site | a. Undosed | 0 | 101 | <5 | <15 | | | | |
| Muscle, 1 inch from Dose Site | a. Undosed | 0 | 102 | <5 | <15 | | | | |
| Muscle, 1 inch from Dose Site | b. Low Topical Dose, Non-abraded Skin | 2 | 201 | 90.5 | 271.5 | 0.84 | 0.7156015672 | 0.84 | 0.5886701779 |
| Muscle, 1 inch from Dose Site | b. Low Topical Dose, Non-abraded Skin | 2 | 202 | 44.2 | 132.6 | | | | |
| Muscle, 1 inch from Dose Site | b. Low Topical Dose, Non-abraded Skin | 4 | 203 | 8.47 | 25.41 | | | | |
| Muscle, 1 inch from Dose Site | b. Low Topical Dose, Non-abraded Skin | 4 | 202 | 8.78 | 26.28 | 1.25 | | 1.25 | |
| Muscle, 1 inch from Dose Site | b. Low Topical Dose, Non-abraded Skin | 4 | 205 | 295 | 885 | | | | |
| Muscle, 1 inch from Dose Site | b. Low Topical Dose, Non-abraded Skin | 4 | 206 | 108 | 333 | 0.87 | | 0.87 | |
| Muscle, 1 inch from Dose Site | b. Low Topical Dose, Non-abraded Skin | 24 | 207 | <5 | <15 | | | | |
| Muscle, 1 inch from Dose Site | c. High Topical Dose, Non-abraded Skin | 2 | 208 | 75.9 | 227.7 | 0.34 | 3.0905078707 | 0.34 | 2.3177390809 |
| Muscle, 1 inch from Dose Site | c. High Topical Dose, Non-abraded Skin | 2 | 303 | 2950 | 8850 | | | | |
| Muscle, 1 inch from Dose Site | c. High Topical Dose, Non-abraded Skin | 2 | 302 | 612 | 1836 | | | | |
| Muscle, 1 inch from Dose Site | c. High Topical Dose, Non-abraded Skin | 4 | 303 | 667 | 2001 | | | | |
| Muscle, 1 inch from Dose Site | c. High Topical Dose, Non-abraded Skin | 4 | 304 | 243 | 729 | 6.75 | | 6.75 | |
| Muscle, 1 inch from Dose Site | c. High Topical Dose, Non-abraded Skin | 4 | 305 | 1200 | 3600 | | | | |
| Muscle, 1 inch from Dose Site | c. High Topical Dose, Non-abraded Skin | 4 | 306 | 135 | 405 | | | | |
| Muscle, 1 inch from Dose Site | c. High Topical Dose, Non-abraded Skin | 4 | 307 | 129 | 387 | 1.58 | | 1.58 | |
| Muscle, 1 inch from Dose Site | c. High Topical Dose, Non-abraded Skin | 24 | 308 | 13.3 | 32.4 | | | | |
| Muscle, 1 inch from Dose Site | d. Low Topical Dose, Abraded Skin | 2 | 403 | <5 | <15 | 0.10 | 0.5475070407 | 0.10 | 1.7789313111 |
| Muscle, 1 inch from Dose Site | d. Low Topical Dose, Abraded Skin | 2 | 404 | 381 | 1143 | | | | |
| Muscle, 1 inch from Dose Site | d. Low Topical Dose, Abraded Skin | 4 | 403 | 90.9 | 92.7 | 0.45 | | 0.45 | |
| Muscle, 1 inch from Dose Site | d. Low Topical Dose, Abraded Skin | 4 | 402 | 30.5 | 91.5 | | | | |
| Muscle, 1 inch from Dose Site | d. Low Topical Dose, Abraded Skin | 4 | 405 | 67.2 | 201.6 | | | | |
| Muscle, 1 inch from Dose Site | d. Low Topical Dose, Abraded Skin | 4 | 406 | 96 | 289 | | | | |
| Muscle, 1 inch from Dose Site | d. Low Topical Dose, Abraded Skin | 4 | 407 | 460 | 1380 | 1.08 | | 1.08 | |
| Muscle, 1 inch from Dose Site | d. Low Topical Dose, Abraded Skin | 24 | 408 | 93.1 | 273.3 | 0.92 | 0.8673683253 | 0.92 | 0.8765540987 |
| Muscle, 1 inch from Dose Site | e. High Topical Dose, Abraded Skin | 2 | 503 | 2450 | 7350 | | | | |
| Muscle, 1 inch from Dose Site | e. High Topical Dose, Abraded Skin | 2 | 504 | 683 | 2049 | 2.36 | | 2.36 | |
| Muscle, 1 inch from Dose Site | e. High Topical Dose, Abraded Skin | 4 | 503 | 76.5 | 229.5 | | | | |
| Muscle, 1 inch from Dose Site | e. High Topical Dose, Abraded Skin | 4 | 502 | 15.9 | 47.7 | | | | |
| Muscle, 1 inch from Dose Site | e. High Topical Dose, Abraded Skin | 4 | 505 | 11.4 | 34.2 | 0.28 | | 0.28 | |
| Muscle, 1 inch from Dose Site | e. High Topical Dose, Abraded Skin | 4 | 506 | 24.7 | 74.1 | | | | |
| Muscle, 1 inch from Dose Site | e. High Topical Dose, Abraded Skin | 4 | 507 | 17.6 | 52.8 | | | | |
| Muscle, 1 inch from Dose Site | e. High Topical Dose, Abraded Skin | 24 | 508 | 168 | 504 | | | | |
| Muscle, 1 inch from Dose Site | f. Intravenous Dose | 2 | 603 | 3640 | 10920 | | | | |
| Muscle, 1 inch from Dose Site | f. Intravenous Dose | 4 | 604 | 87.4 | 263.3 | | | | |
| Muscle, 1 inch from Dose Site | f. Intravenous Dose | 4 | 605 | 79.2 | 237.6 | | | | |
| Muscle, 1 inch from Dose Site | f. Intravenous Dose | 4 | 606 | 1580 | 4740 | | | | |
| Muscle, 1 inch from Dose Site | f. Intravenous Dose | 4 | 607 | 1.13 | 3.39 | | | | |
| Muscle, 1 inch from Dose Site | f. Intravenous Dose | 24 | 607 | 72.3 | 216.9 | | | | |
| Muscle, 1 inch from Dose Site | f. Intravenous Dose | 24 | 608 | 15.4 | 46.2 | | | | |

TOPICAL VANCOMYCIN FORMULATION AND METHODS OF USE

CROSS-REFERENCE TO RELATED APPLICATION

This application claims the benefit of U.S. Provisional Application Ser. No. 62/026,534 filed Jul. 18, 2014, which is incorporated by reference herein in its entirety.

BACKGROUND OF THE INVENTION

The skin serves as an intricate habitat to a plethora of bacteria. These bacteria are generally commensal, symbiotic or parasitic in nature. However, when the natural defense of the skin is breached, altered, or under moist occlusive conditions, the skin can support the growth of pathogenic bacteria, leading to cutaneous infection. Vancomycin is an antibiotic used for the treatment of bacterial infection.

SUMMARY OF THE INVENTION

Provided herein are methods of treating a skin condition caused by bacterial infection at a skin depth, comprising applying to the skin a topical ointment comprising vancomycin hydrochloride as an active ingredient, wherein the topical ointment provides therapeutically effective amount of vancomycin at the skin depth of the bacterial infection.

In some embodiment, the topical ointment comprises about 0.01% to about 10% of vancomycin hydrochloride. In some embodiments, the topical ointment comprises about 0.1% to about 8% of vancomycin hydrochloride. In some embodiments, the topical ointment comprises about 1% to about 5% of vancomycin hydrochloride.

In some embodiments, the skin depth of the bacterial infection is from about 0.05 mm to about 20 mm. In some embodiments, the skin depth of the bacterial infection is from about 0.3 mm to about 15 mm. In some embodiments, the skin depth of the bacterial infection is from about 1 mm to about 10 mm.

In some embodiments, The method of any one of claims 1-7, wherein the topical ointment provides therapeutically effective amount of vancomycin at an epidermis layer. In some embodiments, the topical ointment provides therapeutically effective amount of vancomycin at the epidermis layer at a concentration of at least 10 times higher than the minimum inhibitory concentration (MIC).

In some embodiments, the topical ointment provides therapeutically effective amount of vancomycin at a dermis layer. In some embodiments, the topical ointment provides therapeutically effective amount of vancomycin at the dermis layer at a concentration of at least 10 times higher than the minimum inhibitory concentration (MIC).

In some embodiments, the topical ointment provides therapeutically effective amount of vancomycin at a subcutaneous tissue layer. In some embodiments, the topical ointment provides therapeutically effective amount of vancomycin at the subcutaneous tissue layer at a concentration of at least 10 times higher than the minimum inhibitory concentration (MIC).

In some embodiments, the topical ointment provides therapeutically effective amount of vancomycin into a muscle. In some embodiments, the topical ointment provides therapeutically effective amount of vancomycin into the muscle at a concentration of at least 10 times higher than the minimum inhibitory concentration (MIC).

In some embodiments, the skin condition is a skin or soft tissue bacterial infection. In some embodiments, the skin condition comprises impetigo, ecthyma, Staphylococcal scalded skin syndrome (SSSS), erysipelas, cellulitis, abscess, necrotizing fasciitis, folliculitis, furunculosis, carbunculosis, secondary skin infection, or a combination thereof.

In some embodiments, the condition is caused by or complicated by Gram positive bacteria. In some embodiments, the Gram positive bacteria comprise *Staphylococcus aureus, Staphylococcus epidermidis*, methicillin-resistant *Staphylococcus aureus* (MRSA), methicillin-resistant *Staphylococcus epidermidis* (MRSE), *Steptococcus pyogenes*, and *Steptococcus agalactiae*.

In some embodiments, the condition is caused by or complicated by methicillin-resistant *Staphylococcus aureus* (MRSA). In some embodiments, the condition is caused by or complicated by methicillin-resistant *Staphylococcus epidermidis* (MRSE).

In some embodiments, the topical ointment further comprises a base selected from the group consisting of liquid paraffin, white petrolatum, purified lanolin, gelation hydrocarbon, a polyethylene glycol, hydrophilic ointment base, white ointment base, simple ointment base, and mixtures thereof.

In some embodiments, the topical ointment further comprises an excipient selected from the group consisting of antiseptics, surfactants, stabilizers, alcohols, esters, oils, and mixtures thereof.

In some embodiments, the topical ointment is administered one or more times a day.

In some embodiments, the topical ointment provides reduced systemic exposure to vancomycin hydrochloride as compared to therapeutically effective doses of IV vancomycin.

In some embodiments, the topical ointment is not used to treat infective eye conditions.

In some embodiments, the method further comprises administering to the subject a second therapeutic agent. In some embodiments, the second therapeutic agent comprises vancomycin intravenous. In some embodiments, the second therapeutic agent is administered before, during or after the administration of the topical ointment. In some embodiments in which the second therapeutic agent is used, the topical ointment is administered one or more times a day.

In some embodiments, the individual in need thereof is penicillin-resistant or penicillin-allergic.

In some embodiments, the vancomycin hydrochloride is essentially in the form of micronized particles. In some embodiments, the micronized vancomycin hydrochloride has an average particle size of from about 1 µm to about 100 µm. In some embodiments, the micronized vancomycin hydrochloride has an average particle size of from about 1 µm to about 90 µm. In some embodiments, the micronized vancomycin hydrochloride has an average particle size of from about 1 µm to about 80 µm. In some embodiments, the micronized vancomycin hydrochloride has an average particle size of from about 1 µm to about 75 µm. In some embodiments, the micronized vancomycin hydrochloride has an average particle size of from about 5 µm to about 75 µm. In some embodiments, the micronized vancomycin hydrochloride has an average particle size of from about 10 µm to about 75 µm. In some embodiments, the micronized vancomycin hydrochloride has an average particle size of from about 10 µm to about 60 µm. In some embodiments, the micronized vancomycin hydrochloride has an average particle size of from about 10 µm to about 50 µm. In some embodiments, the micronized vancomycin hydrochloride has an average particle size of from about 10 µm to about 40 µm. In some embodiments, the micronized vancomycin hydrochloride has an average particle size of from about 20 μm to about 30 μm.

Also provided herein is a method of testing susceptibility of vancomycin for treating bacterial infection at a skin depth, comprising: applying to the skin a topical ointment containing vancomycin hydrochloride as an active ingredient, wherein the topical ointment provides therapeutically effective amount of vancomycin at the skin depth of the bacterial infection; and conducting at least one vancomycin susceptibility testing, wherein the susceptibility testing allows determination of susceptibility of vancomycin for treating bacterial infection at the skin depth.

In some embodiments, the topical ointment used in the susceptibility testing is as defined in the methods of treating a skin condition. In some embodiments, the susceptibility testing comprises Kirby-Bauer test, Stokes test, Epsilometer test, agar dilution test, broth dilution test, or a combination thereof. In some embodiments, the susceptibility testing is performed to determine the minimum inhibitory concentration (MIC).

Further provided herein is a method of treating a skin condition caused by bacterial infection at a skin depth, comprising: applying to the skin of a subject a topical ointment comprising vancomycin hydrochloride as an active ingredient to the patient, wherein the topical ointment provides therapeutically effective amount of vancomycin at the skin depth of the bacterial infection; conducting at least one vancomycin susceptibility testing, wherein the susceptibility testing allows determination of susceptibility of vancomycin for treating bacterial infection at the skin depth; and continuing the therapeutic treatment if the patient is susceptible to vancomycin or discontinuing the therapeutic treatment if the patient is resistant to vancomycin.

In some embodiments, the topical ointment used in the susceptibility testing is as defined in the methods of treating a skin condition. In some embodiments, the susceptibility testing comprises Kirby-Bauer test, Stokes test, Epsilometer test, agar dilution test, broth dilution test, or a combination thereof. In some embodiments, the susceptibility testing is performed to determine the minimum inhibitory concentration (MIC).

Further provided herein is a skin ointment composition for treating a skin condition caused by bacterial infection at a skin depth. The composition comprises vancomycin hydrochloride essentially in the form of micronized particles; and an ointment base, wherein the composition provides therapeutically effective amount of vancomycin at the skin depth of the bacterial infection.

In some embodiments, the composition comprises about 0.01% to about 10% of vancomycin hydrochloride. In some embodiments, the composition comprises about 0.1% to about 8% of vancomycin hydrochloride. In some embodiments, the composition comprises about 1% to about 5% of vancomycin hydrochloride.

In some embodiments, the skin depth of the bacterial infection is from about 0.05 mm to about 20 mm. In some embodiments, the skin depth of the bacterial infection is from about 0.3 mm to about 15 mm. In some embodiments, The the skin depth of the bacterial infection is from about 1 mm to about 10 mm.

In some embodiments, the composition provides therapeutically effective amount of vancomycin at an epidermis layer. In some embodiments, the composition provides therapeutically effective amount of vancomycin at the epidermis layer at a concentration of at least 10 times higher than the minimum inhibitory concentration (MIC).

In some embodiments, the composition provides therapeutically effective amount of vancomycin at a dermis layer. In some embodiments, the composition provides therapeutically effective amount of vancomycin at the dermis layer at a concentration of at least 10 times higher than the minimum inhibitory concentration (MIC).

In some embodiments, the composition provides therapeutically effective amount of vancomycin at a subcutaneous tissue layer. In some embodiments, the composition provides therapeutically effective amount of vancomycin at the subcutaneous tissue layer at a concentration of at least 10 times higher than the minimum inhibitory concentration (MIC).

In some embodiments, the composition provides therapeutically effective amount of vancomycin into a muscle. In some embodiments, the composition provides therapeutically effective amount of vancomycin into the muscle at a concentration of at least 10 times higher than the minimum inhibitory concentration (MIC).

In some embodiments, the ointment base is selected from the group consisting of liquid paraffin, white petrolatum, purified lanolin, gelation hydrocarbon, a polyethylene glycol, hydrophilic ointment base, white ointment base, simple ointment base, and mixtures thereof.

In some embodiments, the composition further comprises an excipient selected from the group consisting of antiseptics, surfactants, stabilizers, alcohols, esters, oils, and mixtures thereof.

In some embodiments, the topical ointment provides reduced systemic exposure to vancomycin hydrochloride as compared to therapeutically effective doses of IV vancomycin.

In some embodiments, the micronized vancomycin hydrochloride has an average particle size of from about 1 μm to about 100 μm. In some embodiments, the micronized vancomycin hydrochloride has an average particle size of from about 1 μm to about 90 μm. In some embodiments, the micronized vancomycin hydrochloride has an average particle size of from about 1 μm to about 80 μm. In some embodiments, the micronized vancomycin hydrochloride has an average particle size of from about 1 μm to about 75 μm. In some embodiments, the micronized vancomycin hydrochloride has an average particle size of from about 5 μm to about 75 μm. In some embodiments, the micronized vancomycin hydrochloride has an average particle size of from about 10 μm to about 75 μm. In some embodiments, the micronized vancomycin hydrochloride has an average particle size of from about 10 μm to about 60 μm. In some embodiments, the micronized vancomycin hydrochloride has an average particle size of from about 10 μm to about 50 μm. In some embodiments, the micronized vancomycin hydrochloride has an average particle size of from about 10 μm to about 40 μm. In some embodiments, the micronized vancomycin hydrochloride has an average particle size of from about 20 μm to about 30 μm.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 illustrates the effect of vancomycin (topical) and vancomycin IV in plasma.

FIG. 4 illustrates the effect of vancomycin (topical) and vancomycin IV in the epidermis.

FIG. 5 illustrates the effect of vancomycin (topical) and vancomycin IV in the dermis.

FIG. 6 illustrates the effect of vancomycin (topical) and vancomycin IV in muscle at the dose site.

FIG. 7 illustrates the effect of vancomycin (topical) and vancomycin IV in muscle 1 inch from the dose site.

DETAILED DESCRIPTION OF THE INVENTION

Figure 1:
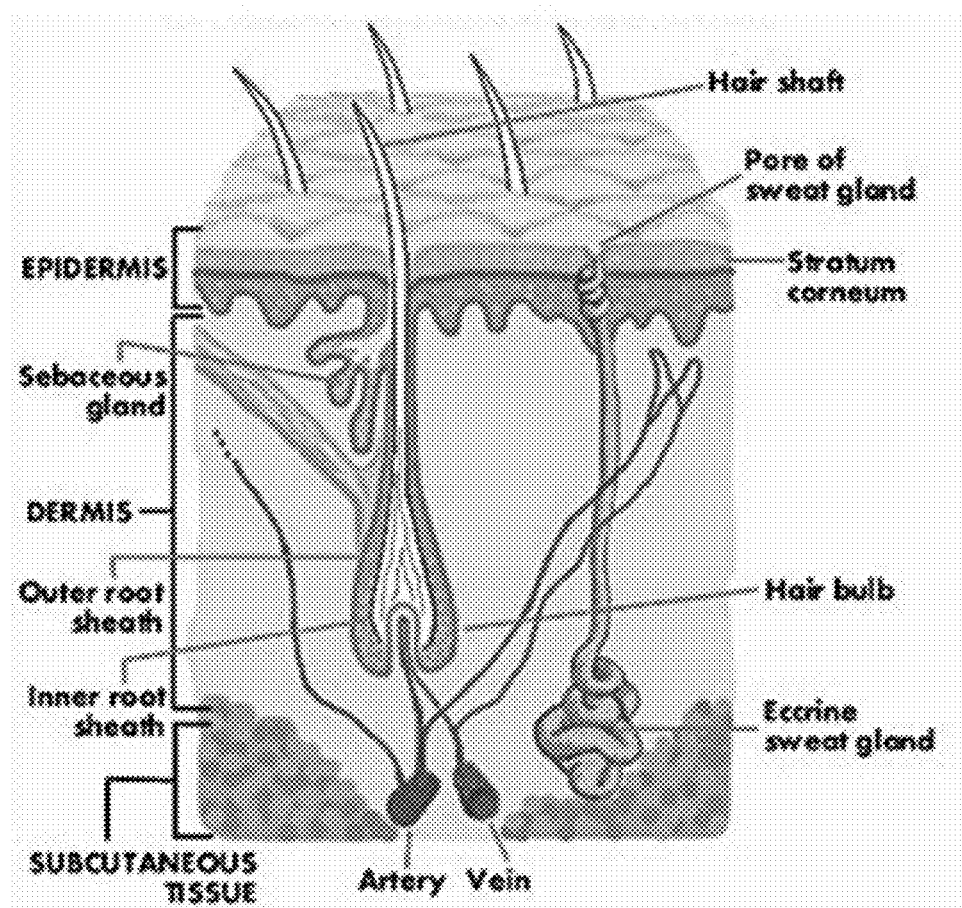
FIG. 1 illustrates a cartoon diagram of the different layers of the skin.

Topical ointment comprising vancomycin as disclosed herein is useful for the treatment of cutaneous skin conditions. The topical ointment disclosed herein is further useful for reducing systemic exposure to vancomycin, for reducing vancomycin exposure time, and reducing the risk or rate of resistance.

Without wishing to be bound by any particular theory, the present disclosure recognizes that while vancomycin has significant antibacterial properties, topical skin formulations have not been developed because of the instability of vancomycin, for example in an ointment formulation or other suitable forms of topical skin formulations. In addition, the present disclosure recognizes that while vancomycin has significant antibacterial properties, topical skin formulations have not been developed for penetration into the depth of the skin where the infections reside. Finally, the present disclosure recognizes that while vancomycin has significant antibacterial properties, topical skin formulations have not been developed for controllable/tunable delivery of vancomycin into the skin to reach various targeted depth.

Disclosed herein, in certain embodiments, is a method of treating a skin condition caused by bacterial infection at a skin depth, comprising applying to the skin a topical ointment comprising vancomycin hydrochloride as an active ingredient, wherein the topical ointment provides therapeutically effective amount of vancomycin at the skin depth of the bacterial infection.

Disclosed herein, in certain embodiments, is a method of testing susceptibility of vancomycin for treating bacterial infection at a skin depth, comprising: (a) applying to the skin a topical ointment containing vancomycin hydrochloride as an active ingredient, wherein the topical ointment provides therapeutically effective amount of vancomycin at the skin depth of the bacterial infection; and (b) conducting at least one vancomycin susceptibility testing, wherein the susceptibility testing allows determination of susceptibility of vancomycin for treating bacterial infection at the skin depth.

Disclosed herein, in certain embodiments, is a method of treating a skin condition caused by bacterial infection at a skin depth, comprising: (a) applying to the skin of a subject a topical ointment comprising vancomycin hydrochloride as an active ingredient to the patient, wherein the topical ointment provides therapeutically effective amount of vancomycin at the skin depth of the bacterial infection; (b) conducting at least one vancomycin susceptibility testing, wherein the susceptibility testing allows determination of susceptibility of vancomycin for treating bacterial infection at the skin depth; and (c) continuing the therapeutic treatment if the patient is susceptible to vancomycin or discontinuing the therapeutic treatment if the patient is resistant to vancomycin.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error.

As used herein "essentially in the form of micronized powder" includes, by way of example only, greater than 70% by weight of the active agent is in the form of micronized particles of the active agent. In further embodiments, the term means greater than 80% by weight of the active agent is in the form of micronized particles of the active agent. In yet further embodiments, the term means greater than 90% by weight of the active agent is in the form of micronized particles of the active agent. The term "micronized" refers to the size of the particles as described herein, and does not limit the particles by the process of its manufacturing. In other words, the "micronized" particles should cover both particles obtained through size-reduction and particles obtained without size-reduction.

The terms "effective amount" or "therapeutically effective amount," as used herein, refer to a sufficient amount of the vancomycin being delivered that would be expected to relieve to some extent one or more of the symptoms of the disease or condition being treated. For example, the result of administration of vancomycin disclosed herein is reduction and/or alleviation of the signs, symptoms, or causes of skin infection. For example, an "effective amount" for therapeutic uses is the amount of vancomycin, including a formulation as disclosed herein required to provide a decrease or amelioration in disease symptoms without undue adverse side effects. The term "therapeutically effective amount" includes, for example, a prophylactically effective amount. An "effective amount" of vancomycin disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate release dosing format based upon pharmacokinetic and pharmacodynamic considerations.

As used herein, the term "stabilizers" refers to compounds such as any antioxidation agents, buffers, acids, preservatives and the like that are compatible with the environment of the middle or inner ear. Stabilizers include but are not limited to agents that will do any of (1) improve the compatibility of excipients with a container, or a delivery system, including a syringe or a glass bottle, (2) improve the stability of a component of the composition, or (3) improve formulation stability.

As used herein, the term "subject" is used to mean an animal, preferably a mammal, including a human or non-human. The terms patient and subject may be used interchangeably.

The terms "treat," "treating" or "treatment," as used herein, include alleviating, abating or ameliorating a disease or condition, for example tinnitus, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "Gram-positive bacteria" refers to a class of bacteria that take up the crystal violet stain used in the Gram staining method of bacterial differentiation. Exemplary Gram-positive bacteria include, but are not limited to, *Staphylococcus aureus, Staphylococcus epidermidis, Staphylococcus saprophyticus, Streptococcus pneumonia, Streptococcus pyogenes, Streptococcus agalactiae, Enterococcus avium, Enterococcus durans, Enterococcus faecium, Enterococcus gallinarum, Enterococcus hirae, Enterococcus solitarius, Bacillus anthracis, Bacillus oereus, Bifidobacteriu bifidum, Lactobacillus* sp. *Listeria monocytogenes, Nocardia* sp. *Rhodococcus equi, Actinomyces* sp. *Clostridium botulinum, Clostridium difficile, Clostridium perfringens, Clostridum tetani, Mobiluncus* sp. and *Peptostreptococcus* sp.

The section headings used herein are for organizational purposes only and are not to be construed as limiting the subject matter described.

Cutaneous Infection Overview

Cutaneous infection is characterized as an infection of the skin. In some embodiments, cutaneous infection is caused or complicated by Gram-positive bacteria. In some embodiments, the Gram-positive bacteria include *Staphylococcus aureus, Staphylococcus epidermidis, Staphylococcus saprophyticus, Steptococcus pyogenes,* and *Steptococcus agalactiae*. In some embodiments, cutaneous infection is caused or complicated by *Staphylococcus aureus, Staphylococcus epidermidis, Staphylococcus saprophyticus, Steptococcus pyogenes, Steptococcus agalactiae,* or a combination thereof. In some embodiments, cutaneous infection is caused or complicated by *Staphylococcus aureus*. In some embodiments, cutaneous infection is caused or complicated by *Staphylococcus epidermidis*. In some embodiments, the *Staphylococcus aureus* is a methicillin-resistant *Staphylococcus aureus* (MRSA). In some embodiments, the *Staphylococcus epidermidis* is a methicillin-resistant *Staphylococcus epidermidis* (MRSE). In some embodiments, cutaneous infection is caused or complicated by methicillin-resistant *Staphylococcus aureus* (MRSA). In some embodiments, cutaneous infection is caused or complicated by methicillin-resistant *Staphylococcus epidermidis* (MRSE). In some embodiments, cutaneous infection is caused or complicated by *Steptococcus pyogenes*. In some embodiments, cutaneous infection is caused or complicated by *Steptococcus agalactiae*. In some embodiments, the Steptococcus *pyogenes* is a group A β-hemolytic *streptococcus* (GAS). In some embodiments, the *Steptococcus agalactiae* is a group B streptococcus (GBS).

MRSA, also known as the "Super Bug", is a bacterium that is responsible for many difficult-to-treat infections in humans. In general, MRSA refers to any strains of *Staphylococcus* that has developed either through natural selection or acquired resistance to β-lactams including penicillins and cephalosporins. Although resistance does not cause the bacteria to become intrinsically more virulent, however, due to the natural of ineffectiveness to most standard types of antibiotics, MRSA is more difficult to treat. Initial presentation of MRSA includes mild skin infections such as pimples or boils in different areas of the body. In some cases, fever and occasional rash may accompany MRSA infection. After 72 hours, MRSA can be established into the tissue and become resistant to treatment. Within a few days, these pimples or boils become larger and more painful, and eventually advance into deep, pus-filled boils. In some cases, infections can lead to serious skin infections spreading into the bloodstream, surgical wounds, or internal organs, which can be life-threatening.

MRSE, similar to MRSA, is a resistant variation of the *Staphylococcus epidermidis*. Like MRSA, MRSE is resistant to several subgroups of β-lactams including penicillins and cephalosporins.

Methicillin-resistant bacteria such as MRSA and MRSE are not only difficult to treat, but also costly to treat. Indeed, one study analyzed 1,131 MRSA patients and 1,587 patients with drug-sensitive *Staphylococcus aureus*. Due to the multidrug resistant nature of MRSA, the study indicated that all MRSA patients had a worse clinical outcome when compared to non-MRSA patients. Further, the study indicated that these patients were 36% more likely to die, or stayed in the hospital seven days longer, and their associated hospital costs were $7,250 to $11,500 higher than their counterparts. Furthermore, the study predicted that if MRSA would replace drug-sensitive *Staphylococcus aureus*, then there would be an additional 2,700 cases of death annually, 210,000 days of hospitalization, and $310 million in hospital expenditures.

First-line treatment for MRSA often fails to kill the bacteria. As a result, vancomycin is generally prescribed and has been considered as the reference standard for treatment of MRSA. Vancomycin can be administered orally or intravenously. Oral administration generally lead to poor absorption of the drug into the body, therefore, intravenous administration has been the predominate choice.

With either routes of administration, the concentration that is delivered into the target site and the concentration needed to eradicate the bacteria are important for determining the clinical success of the treatment. For example, a minimum inhibitory concentration (MIC) is generally determined, which indicates the minimum concentration of antibiotic needed to inhibit a bacterium. To achieve eradication of the bacterium, a concentration at the target site is proposed to be about 10-12 times the MIC. However, for some strains of MRSA and other bacteria such as MRSE which have high MICs, the antibiotic concentrations required to eradicate the bacteria would either lead to toxicity, or that if a lower concentration is administered, would yield sub-optimal levels. Long-term exposure to sub-optimal antibiotic levels would induce the emergence of resistance. Therefore, an alternative treatment is needed.

Disclosed herein, in certain embodiments, are methods of treating a skin condition caused by bacterial infection at a skin depth, comprising applying to the skin a topical ointment comprising vancomycin hydrochloride as an active ingredient, wherein the topical ointment provides therapeutically effective amount of vancomycin at the skin depth of the bacterial infection. Also disclosed herein, in certain embodiments, are methods of treatment, comprising a combination of a topical ointment comprising vancomycin hydrochloride as an active ingredient and a second therapeutic agent.

Additional disclosures include methods of testing susceptibility of vancomycin for treating bacterial infection at a skin depth, comprising: (a) applying to the skin a topical ointment containing vancomycin hydrochloride as an active ingredient, wherein the topical ointment provides therapeutically effective amount of vancomycin at the skin depth of the bacterial infection; and (b) conducting at least one vancomycin susceptibility testing, wherein the susceptibility testing allows determination of susceptibility of vancomycin for treating bacterial infection at the skin depth.

Further disclosed herein, in certain embodiments, is a method of treating a skin condition caused by bacterial infection at a skin depth, comprising: (a) applying to the skin of a subject a topical ointment comprising vancomycin hydrochloride as an active ingredient to the patient, wherein the topical ointment provides therapeutically effective amount of vancomycin at the skin depth of the bacterial infection; (b) conducting at least one vancomycin susceptibility testing, wherein the susceptibility testing allows determination of susceptibility of vancomycin for treating bacterial infection at the skin depth; and (c) continuing the therapeutic treatment if the patient is susceptible to vancomycin or discontinuing the therapeutic treatment if the patient is resistant to vancomycin.

The Skin

The skin is an ever-changing organ that contains numerous specialized cells and structures. It functions as a protective barrier that interfaces with a sometimes-hostile environment. Further, it aids in maintaining the proper temperature for the body to function. The skin gathers sensory information from the environment, and plays an active role in the immune system as a defense barrier from diseases.

The skin is comprised of three layers: an epidermis layer, a dermis layer, and a subcutaneous tissue layer (FIG. 1). The epidermis is the outer layer of skin. Its thickness varies in different types of skin. It is the thinnest on the eyelids at about 0.05 mm and the thickest on the palms and soles at about 1.5 mm. The epidermis contains 5 layers. From the inner layer to the outer layer, they are stratum basale, stratum spinosum, stratum granulosum, stratum licidum and stratum corneum. The stratum basale layer comprises of cells that are shaped like columns. In this layer the cells divide and push already formed cells into higher layers. As the cells move into the higher layers, they flatten and eventually die. The outer layer of the epidermis, the stratum corneum, comprises of dead, flat skin cells that shed about every 2 weeks.

The dermis varies in thickness depending on the location of the skin. It is about 0.3 mm on the eyelid and about 3.0 mm on the back. The dermis comprises of three types of tissue that are heterogenous in nature and are not confined into layers. The types of tissue include collagen, elastic tissue, and reticular fibers. The dermis is further stratified into two layers, a papillary layer and a reticular layer. The upper papillary layer contains a thin arrangement of collagen fibers. The lower reticular layer is thicker than the papillary layer, and comprises of thick collagen fibers that are arranged parallel to the surface of the skin.

The subcutaneous tissue is a layer of fat and connective tissue that houses larger blood vessels and nerves. This layer is important for the regulation of temperature of the skin itself and the body. The size of this layer varies throughout the body and from person to person.

Skin Conditions

Initial symptoms of cutaneous infections are generally characterized as pimples or boils. When untreated, these infections progress and may lead to deeper tissue damage. There are several conditions or disease associated with bacterial infection. They include impetigo, ecthyma, Staphylococcal scalded skin syndrome (SSSS), erysipelas, cellulitis, abscess, necrotizing fasciitis, folliculitis, furunculosis, carbunculosis, and secondary skin infections.

Impetigo

Impetigo is a contagious skin infection caused by *S. aureus* and occasionally caused by *S. pyogenes*. Impetigo occurs predominately in infants and children, affecting approximately 1% of children. There are two clinical types of impetigo, nonbullous and bullous. Nonbullous impetigo accounts for more than 70% of cases, occurring on the face and extremities, initially with vesicle or pustules on reddened skin. The vesicles or pustules then rupture leaving a characteristic honey-colored crust. Bullous impetigo comprises larger flaccid bullae with clear yellow fluid, when ruptures leave a thin, smooth, golden-yellow crust.

In general, treatment comprises first-line topical treatment such as retapamulin and mupirocin ointment or systemic therapy including dicloxacillin, amoxicillin plus clavulanic acid, cephalexin and oxacycline. Second-line treatment includes azithromycin, clindamcin and erythromycin. In some embodiments, complications arise and include scarring, ecthyma, cellulitis, or kidney damage.

Ecthyma

Ecthyma is a pyogenic infection caused by *S. aureus* and *S. pyogenes*. It is characterized by an initial lesion consisting of an erythematous plague, measuring 2 to 3 cm in diameter. Next, a vesicle or vesiculopustule develops and ruptures, forming a superficial ulcer with hard, thick, honey-colored crusts. In general, the border of the ulcer is indurated and violaceous, and the granular tissue extends into the dermis. Ecthyma typically occurs in poor hygienic environments, but can also be resulted from neglected impetigo. The infection can occur on sites of insect bites, lesions or scabies or pruriginous dermatosis. Further, these lesions generally occur in the legs, feet, thighs and buttocks.

In general, first-line treatment comprises dicloxacillin, amoxicillin with clavulanic acid, clavulanic acid alone, or cephalexin. Second-line treatment includes azithromycin, clindamycin and erythromycin.

Staphylococcal Scalded Skin Syndrome (SSSS)

Staphylococcal scalded skin syndrome (SSSS), also known as Ritter's disease, Pemphigus neonatorum, or Localized bullous impetigo, is a cutaneous condition caused by the toxins produced by *Staphylococcus aureus*. SSSS primarily occur in children, due to their lack of immunity to toxins as well as their kidney immaturity thereby leading to poor elimination of toxins. In adults, SSSS is associated with underlying diseases related to immunosuppression, altered immunity and renal insufficiency. There are two forms of enterotoxins, toxin A (ET A) and toxin B (ET B), with ET B as the predominant isoform.

Initial infection occurs as otitis, conjunctivitis, or other forms of infection. After the initial onset, fever and diffuse erythema appear, in which flaccid blisters develop and rapidly ruptures, resulting in large areas of erosion surrounded by epidermal patches, corresponding to detached skin. Further, Nikolsky's sign is present, i.e. when a gentle rubbing of the skin results in exfoliation of the outermost skin layer. There is no mucosal involvement and clearing occurs in 7 to 10 days.

In general, treatment comprises administration of semi-synthetic penicillins such as oral or intravenous oxacillin or alternatives such as linezolid and quinupristin-dalfopristin. Further, daptomycin, flucloxacillin, or topical therapies such as mupirocin and retapamulin are suitable first-line treatments as well.

Erysipelas

Erysipelas is an acute inflammatory skin infection involving the dermal lymphatic vessels. It is generally caused by group A β-hemolytic streptococcus, although in some cases, is caused by *Staphylococcus aureus* as well. Erysipelas primarily affects adults between 40-60 years of age. It affects predominantly the lower limbs, although in certain cases, it affects the facial region as well.

In general, erysipelas is characterized by a single elevated lesion, about 10 to about 15 cm in its largest axis, with a clear border. In certain cases, the clear border advances with the progression of the condition. Flaccid blisters, in some cases, may develop, which contains translucent content. Fever, chills, malaise, and oftentimes nausea or vomiting also accompany erysipelas.

Erysipelas treatments include first-line treatment such as penicillin and dicloxacillin, and second-line treatment include linezolid, vancomycin, and clindamycin.

Cellulitis

Cellulitis is a cutaneous infection that extends to the subcutaneous layer. It is generally caused by *Staphylococcus aureus*. Cellulitis is characterized by a redness at the site of infection with the size of affected area increasing with time. The borders of the area of redness are not sharply defined, and the skin is generally swollen and painful to the touch. Often, this infection is accompanied by fever. The most common sites involved are the upper and lower limbs and the face.

Cellulitis treatments are similar to the treatments for erysipelas. First-line treatment comprises dicloxacillin and amoxicillin with clavulanic acid; whereas second-line treatment comprises linezolid, vancomycin, azithromycin, clindamycin and erythromycin. In severe cases, removal of dead tissue is required.

Necrotizing Fasciitis

Necrotizing fasciitis is a rare infection of the subcutaneous tissues and fascia that eventually leads to necrosis. In general, *Streptococcus pyogenes* is the predominant cause of necrotizing fasciitis, however, other bacteria such as group B streptococcus (GBS) and MRSA can also induce necrotizing fasciitis. Initial presentation of infection is warm, tender, inflamed skin that rapidly extends outward. Within 48 to 72 hours, affected skin becomes dusky, with formation of bullae, followed by necrosis, gangrene and often with crepitus. Necrotizing fasciitis commonly occurs on the extremities, abdomen, perineum, or at operative wounds. It is a surgical emergency requiring debridement, fasciotomy and amputation in some cases. Parenteral antibiotics such as gentamicin and clindamycin are required as well.

Abscess

Abscess is a collection of pus built up with the skin layers. It is caused by different types of bacteria, including *Staphylococcus* and *Streptococcus* strains. It is characterized by redness, inflammation, swelling and pain at the site of infection. Carbuncles and furuncles are types of abscess involving hair follicles. In general, treatment involves incision and drainage. Different classes of antibiotics are also used, depending on the type of bacterial infection.

Folliculitis, Furunculosis, and Carbunculosis

Folliculitis is an inflammation of the hair follicle generally caused by *Staphylococcus aureus*. It is defined by a presence of inflammatory cells in the inner wall and ostium of the hair follicles, thereby creating a follicular pustule. In some cases, the inflammation is superficial or confined to the upper portion of the hair follicles. In other cases, the inflammation extends to the entire hair follicle. Superficial folliculitis, also known as impetigo of Bockhart, is characterized by small fragile pustules that occur in the infundibulum of hair follicles. Pseudofolliculitis is a papulopustular acneiform eruption on the beard area. It is generally characterized with inflamed papuleus, and in some cases, pustules can form if the area becomes infected. Similar to pseudofolliculitis, sycosis barbae is a deep folliculitis with perifollicular inflammation occurring in the beard area. Nuchal keloid folliculitis is characterized by deep folliculitis with scarring or perifoliculitis. It occurs in the posterior, inferior occipital and the nuchal region of the neck. Folliculitis decalvans is a form of chronic folliculitis, which leads to destruction of follicles, resulting in scarring alopecia. Furuncle, or boil, is a nodule in a hair-bearing area that discharges purulent, necrotic debris. Carbuncles are multiple furuncles that coalesce to form large, deep, interconnected abscesses.

In general, first-line treatments for folliculitis include topical therapy with clindamycin or erythromycin, or antibiotic wash such as chlorhexidine. Second-line treatments for folliculitis include doxycycline. For furunculosis and carbunculosis, first-line treatments include dicloxacillin, amoxicillin with calvulanic acid, calvulanic acid alone, or cephalexin. Second-line treatments for furunculosis and carbunculosis include coxycycline and vancomycin.

Secondary Skin Infections

In some embodiments, secondary skin infections occur due to an underlying condition or illness. In some embodiments, the underlying condition or illness include, but is not limited to, severe atopic dermatitis, diabetes, kidney disorder, blood disorder such as leukaemia and lymphoma, malnutrition, inflammatory diseases such as psoriasis, AIDS, pre-existing wounds, burns, or a combination thereof. In some embodiments, treatment is tailored to the specific pathogen or combination of pathogens.

Susceptibility Testing and Therapeutic Drug Monitoring Parameters

Susceptibility testing is a test that determines the likelihood of a particular antimicrobial treatment is effective in stopping the growth of a target pathogen. In some embodiments, the term susceptibility is used to refer to when pathogens such as bacteria are unable to grow in the presence of one or more antimicrobial drugs. In general, susceptibility testing is primarily performed on bacteria, but can also be performed on fungi. Testing determines the potential effectiveness of the specific antimicrobial treatment or specific combination of antimicrobial treatments on the pathogen (e.g. bacteria) and/or determines if the pathogen (e.g. bacteria) has developed resistance. In some embodiments, testing is also performed on viruses to determine their resistance to antiviral drugs. However, the procedure involved in testing viruses differs from that for bacteria and fungi.

Disclosed herein, in certain embodiments, is a method of optimizing a therapeutic treatment, comprising: (a) administering a topical ointment comprising vancomycin hydrochloride as an active ingredient to the patient if the patient is susceptible to vancomycin hydrochloride; (b) conducting a susceptibility testing to the patient; and (c) continuing the therapeutic treatment if the patient is susceptible to vancomycin hydrochloride or discontinuing the therapeutic treatment if the patient is resistant to vancomycin hydrochloride. Also disclosed herein, in certain embodiments, is a method of selecting a patient having a skin condition caused by a bacterial infection as a candidate for treatment with a topical ointment comprising vancomycin hydrochloride as an active ingredient, comprising conducting at least one susceptibility testing; and characterize the patient as a candidate for treatment if the patient is susceptible to vancomycin hydrochloride.

In some embodiments, a pathogen is identified prior to subjecting to a susceptibility testing. In brief, a sample is collected from the site of an infection and then cultured to isolate one or more pathogens. The one or more pathogens are then identified using biochemical, enzymatic, or molecular tests. Exemplary biochemical, enzymatic, or molecular tests include, but are not limited to, catalase test, mannitol salt agar (MSA), blood agar plates (BAP), Streak-stab technique, Taxos P (optochin sensitivity testing), Taxos A (bacitracin sensitivity testing), CAMP test, bile esculin agar, nitrate broth, spirit blue agar, starch hydrolysis test, motility agar, coagulase test, nucleic acid amplification-based tests such as polymerase chain reaction (PCR), nucleic acid probe-based assays, hybridization based assays such as fluorescent in situ hybridization (FISH), or mass spectrometry methods such as matrix assisted laser desorption ionization time-of-flight mass spectrometry (MALDI-ToF MS). Next, a susceptibility testing is performed on each type of the pathogens isolated and identified.

In some embodiments, susceptibility testing is performing using one or more testing methods. In some embodiments, these methods include Kirby-Bauer method (disk diffusion method), Stokes method, Epsilometer test, agar dilution, broth dilution, and tests utilizing automated instrumentations. In some embodiments, an antibiogram or a report that details the susceptibility testing is generated. In some embodiments, the test result is categorized as susceptible, intermediate, or resistance. In some embodiments, MIC is determined from these tests.

In some embodiments, susceptibility testing is performed using the Kirby-Bauer method or the disk diffusion method. This procedure comprises placing small wafers impregnated with antibiotics onto a plate containing a bacterial lawn ($1\text{-}2\times 10^8$ CFU/ml to the surface of a 150 mm diameter Mueller-Hinton agar plate). The plate is then incubated for 16-24 hours at 35° C. If the bacteria are sensitive to the antibiotic, a clear ring is observed around the wafer, which indicates inhibition of bacterial growth. These rings are measured to the nearest millimeter, and the ring diameters are interpreted using known criteria such as those published by the Clinical and Laboratory Standards Institute (CLSI). The result is qualitative, and is categorized as susceptible, intermediate, or resistance. MIC is generally not calculated, although in some cases, can be approximated. The agar used is Mueller-Hinton agar, with pH between 7.2-7.4.

In some embodiments, susceptibility testing is performed using the Stokes method. This procedure comprises inoculating a control bacterium on a portion of an agar plate while the remainder portion is inoculated with the test bacterium. Disks impregnated with antibiotics are places at the interface to allow comparison of the zones of inhibition.

In some embodiments, antibiotic sensitivity is performed using the Epsilometer test or E-test. E-test is an agar diffusion method (bioMérieux AB Biodisk). In some embodiments, the E-test comprises a test strip which is impregnated with a target antimicrobial drug on its underside and has a scale printed on the upper surface. The test strip is laid on top of an agar plate containing a lawn of bacteria. The antimicrobial drug diffuses into the agar, thereby producing a gradient. After 24 hours incubation, an elliptical zone of inhibition is produced. The intersection of the lower part of the ellipse shaped growth inhibition area and the test strip indicates the MIC of the antimicrobial drug.

In some embodiments, susceptibility testing is performed using the agar dilution test. The agar dilution test comprises incubating two-fold dilutions of antibiotics with bacteria on an agar plate overnight. In general, the antibiotics are impregnated on disks or paper strips prior to placing onto the agar plate. The lowest concentration of antimicrobial agent with no visible growth indicates the MIC.

In some embodiments, susceptibility testing is performed using the broth dilution test. The broth or tube dilution test is one of the earliest susceptibility testing methods. This procedure comprises preparing a two-fold dilution of antibiotics (e.g. 1, 2, 4, 8, and 16 µg/mL) in a liquid growth medium dispended in test tubes. These tubes are then inoculated with a standardized bacterial suspension of $1\text{-}5\times 10^5$ CFU/mL. After overnight incubation at 35° C., the tubes are visually examined for presence of bacterial growth evidenced by turbidity. The lowest concentration of antibiotic that prevents bacterial growth indicates the MIC.

In some embodiments, susceptibility testing is performed using automated instrumentations. In some embodiments, the automated instrumentations include the MicroSacn Walk-Away (Siemens Healthcare Diagnostics), the BD Phoenix Automated Microbiology System (BD Diagnostics), the Vitek 2 System (bioMérieux), and the Sensititre ARIS 2X (Trek Diagnostic Systems). The MicroSacn WalkAway is a self-contained incubator/reader device that can incubate and analyze 40-96 microdilution trays. Turbidimetric end points are read in about 4.5-18 hours. The DB Phoenix Automated Microbiology System is an incubator reader with a capacity to process 99 test panels comprising 84 wells for antibiotic doubling dilutions. Turbidimetric and colorimetric readings are used to detect bacterial growth. MIC readings are generated in 6-16 hours. The Vitek 2 System utilizes compact plastic reagent cards that contain microliter quantities of antibiotics and test media in 64-well format. Similar to the previous devices, it uses turbidimetric monitoring of bacterial growth. Results are generated in about 4-10 hours. The Sensititre ARIS 2X is an automated, overnight, incubator/reader with 64 panel capacity. Each test panel is in 96 well format. Bacterial growth is monitored by fluorescence.

In some embodiments, the results from a susceptibility testing are interpreted using standardized guidelines from the Clinical and Laboratory Standards Institute (CLSI). The results are categorized as susceptible, intermediate, or resistance. In general, a susceptible result indicates that the pathogen is responsive to therapy using the dosage recommended normally for a particular type of infection caused by the pathogen. An intermediate result indicates that the pathogen may be responsive to a higher dose or a more frequent dose of therapy, or that only at a specific site in which the antibiotic penetration provides adequate concentration. A resistance result indicates that the pathogen is not responsive to therapy using the dosages normally prescribed for a particular drug.

In some embodiments, MIC is determined from a susceptibility test. MIC refers to the lowest concentration of an antimicrobial that will inhibit the visible growth of a pathogen after overnight incubation. In some embodiments, the MIC of a pathogen for an antimicrobial (e.g. antibiotics) is about 0.5 mg/L, about 1 mg/L, about 1.5 mg/L, about 2 mg/L, about 2.5 mg/L, about 3 mg/L, about 3.5 mg/L, about 4 mg/L, about 4.5 mg/L, about 5 mg/L or more. In some embodiments, there is a significant relationship between the levels of antimicrobial (e.g. antibiotics) in the target tissues and the MIC of the target organism. In some embodiments, the target ratio for clinical success for most antimicrobial (e.g. antibiotics) is a concentration of at least 6 times to at least 20 times higher, at least 8 times to at least 18 times higher, at least 10 times to at least 16 times, or at least 12 times to at least 16 times higher than the MIC of the target organism. While MIC indicates the potency of an antibiotic, it does not indicate the time course of antimicrobial activity.

Figure 2:
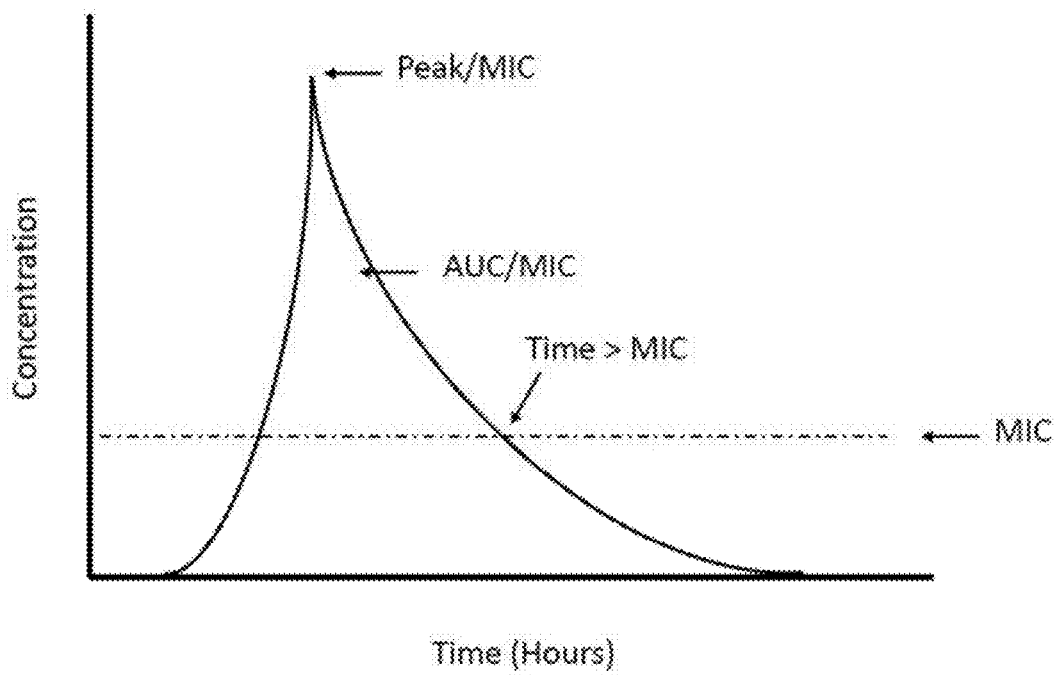
FIG. 2 illustrates a conceptual diagram of pharmacokinetic/pharmacodynamic parameters for predicting antibiotic efficacy.

In some embodiments, additional parameters are utilized to predict the efficacy of an antimicrobial (e.g. antibiotic). In some embodiments, pharmacokinetic (PK) parameters are determined. PK comprises a set of parameters that indicate the time course of antimicrobial concentrations in the body. The relationship between these concentrations and the antimicrobial (e.g. antibiotics) effect establishes the parameters for pharmacodynamics (PD). In some cases, PK parameters include the peak level ($C_{max}$), the trough level ($C_{min}$) or the lowest level that a drug reaches prior to the administration of the next dose, and the Area Under the Curve (AUC). Although these parameters indicate the serum level time course, they do not describe the killing activity of the antimicrobial (e.g. antibiotic). Therefore, integration of the PK parameters with the MIC yields PK/PD parameters that quantify the activity of an antimicrobial (e.g. antibiotic): the peak/MIC ($C_{max}$/MIC) ratio, the T>MIC, and the 24 h AUC/MIC ratio (FIG. 2). In some embodiments, the peak/MIC ratio is a concentration-dependent parameter. In some embodiments, the T>MIC is a time-dependent parameter. In some embodiments, the peak/MIC ($C_{max}$/MIC) ratio, the T>MIC, and the 24 h AUC/MIC ratio are utilized to determine the efficacy of a drug. In some embodiments, the peak/MIC ($C_{max}$/MIC) ratio, and the 24 h AUC/MIC ratio are utilized to determine the efficacy of a drug. In some embodiments, the peak/MIC ($C_{max}$/MIC) ratio is utilized to determine the efficacy of a drug. In some embodiments, the T>MIC is utilized to determine the efficacy of an antimicrobial (e.g. antibiotic) drug. In some embodiments, the 24 h AUC/MIC ratio is utilized to determine the efficacy of an antimicrobial (e.g. antibiotic) drug.

In some embodiments, the peak to MIC ratio is utilized to indicate efficacy in clinical response rate. In some embodiments, a peak of about 6 times to about 20 times, about 8 times to about 18 times, about 10 times to about 16 times, about 12 times to about 14 times the MIC is targeted. In some embodiments, a peak of about 8 times to about 12 times the MIC is targeted. In some embodiments, an approximate 90% response rate is achieved with a peak to MIC ratio of about 8 to about 12.

In some embodiments, the AUC/MIC ratio is utilized to indicate efficacy in clinical response rate. In some embodiments, AUC/MIC ratio is about 120, about 125, about 130, about 135, about 140, about 150, about 160, about 170, about 180, about 190, about 200, about 250, about 300, about 350, about 400, about 450, about 500, or more.

In some embodiments, the T>MIC is utilized to indicate efficacy in clinical response rate. In some embodiments, the T>MIC is about 60%, about 65%, about 70%, about 75%, about 80%, about 85%, about 90%, about 95%, about 99%, or more of the dosing interval.

In some embodiments, the trough concentration is utilized to indicate efficacy in clinical response rate. In some embodiments, when the MIC is less than 1 mg/L, the target trough concentration is from about 8 mg/L to about 20 mg/L, about 10 mg/L to about 18 mg/L, or about 12 mg/L to about 15 mg/L. In some embodiments, when the MIC is greater than 1 mg/L, the target trough concentration is from about 8 mg/L to about 20 mg/L, about 10 mg/L to about 18 mg/L, or about 12 mg/L to about 15 mg/L.

In some embodiments, the pharmacodynamic properties of antimicrobials (e.g. antibiotics) have different patterns of activity. In some embodiments, the patterns of activity is categorized into types I, II and III. Type I activity refers to antimicrobials (e.g. antibiotics) that are concentration-dependent killing with prolonged persistent effects. This type of antimicrobials (e.g. antibiotics) utilizes 24-AUC/MIC and Peak/MIC parameters to determine efficacy. Type II activity refers to antimicrobials (e.g. antibiotics) that are time-dependent killing with minimal persistent effects. This type of antimicrobials (e.g. antibiotics) utilizes T>MIC parameter to determine efficacy. Type III activity refers to antimicrobials (e.g. antibiotics) that are time-dependent killing with moderate to prolonged persistent effects. This type of antimicrobials (e.g. antibiotics) utilizes 24-AUC/MIC parameter to determine efficacy.

Vancomycin is a tricyclic glycopeptides that inhibits bacterial cell wall synthesis. In some embodiments, the MIC for vancomycin is about 0.5 mg/L, about 1 mg/L, about 1.5 mg/L, about 2 mg/L, about 2.5 mg/L, about 3 mg/L, about 3.5 mg/L, about 4 mg/L, about 4.5 mg/L, about 5 mg/L or more. In some embodiments, vancomycin is used to treat methicillin resistant strains such as MRSA and MRSE. In some embodiments, the MIC for vancomycin against MRSA is about 0.5 mg/L, about 1 mg/L, about 1.5 mg/L, about 2 mg/L, about 2.5 mg/L, about 3 mg/L, about 3.5 mg/L, about 4 mg/L, about 4.5 mg/L, about 5 mg/L or more. In some embodiments, the MIC for vancomycin against MRSE is about 0.5 mg/L, about 1 mg/L, about 1.5 mg/L, about 2 mg/L, about 2.5 mg/L, about 3 mg/L, about 3.5 mg/L, about 4 mg/L, about 4.5 mg/L, about 5 mg/L or more.

In some embodiments, a patient having a bacterial infection has a vancomycin MIC of about 0.5 mg/L, about 1 mg/L, about 1.5 mg/L, about 2 mg/L, about 2.5 mg/L, about 3 mg/L, about 3.5 mg/L, about 4 mg/L, about 4.5 mg/L, about 5 mg/L or more. In some embodiments, a patient has a vancomycin MIC of about greater than 1.5 mg/L is associated with a worse disease outcome. In some embodiments, a patient has a vancomycin MIC of about less than 1.5 mg/L is associated with a higher rate of recovery.

In some embodiments, vancomycin is a type III antibiotic. It has both time-dependent killing and moderate to prolonged persistent effects. In some embodiments, the persistent effect include the post-antibiotic effect (PAE), which is the phenomenon of continued suppression of bacterial growth after a short exposure of bacteria to antimicrobial agents.

In some embodiments, 24 h-AUC/MIC ratio is used to correlate with efficacy. In some embodiments, the 24 h-AUC/MIC ratio is about 120, about 125, about 130, about 135, about 140, about 150, about 160, about 170, about 180, about 190, about 200, about 250, about 300, about 350, about 400, about 450, about 500, or more for vancomycin.

In some embodiments, a peak/MIC ratio is also used to correlate with clinical success. In some embodiments, a peak of about 6 times to about 20 times, about 8 times to about 18 times, about 10 times to about 16 times, about 12 times to about 14 times the MIC is targeted. In some embodiments, a peak of about 8 times to about 12 times the MIC is targeted.

In some embodiments, a trough concentration is used to correlate with clinical success. In some embodiments, when the MIC is less than 1 mg/L, the target trough concentration is from about 8 mg/L to about 20 mg/L, about 10 mg/L to about 18 mg/L, or about 12 mg/L to about 15 mg/L. In some embodiments, when the MIC is less than 1 mg/L, the target trough concentration is from about 10 mg/L to about 15 mg/L. In some embodiments, when the MIC is greater than 1 mg/L, the target trough concentration is from about 8 mg/L to about 20 mg/L, about 10 mg/L to about 18 mg/L, about 12 mg/L to about 15 mg/L, or about 15 mg/L to about 20 mg/L. In some embodiments, when the MIC is greater than 1 mg/L, the target trough concentration is from about 15 mg/L to about 20 mg/L.

In some embodiments, resistance occurs through natural selection or through long-term exposure of bacteria to suboptimal antibiotic levels. In some embodiments, resistance is monitored using Kirby-Bauer method (disk diffusion method), Stokes method, Epsilometer test, agar dilution, broth dilution, or a combination thereof. In some embodiments, resistance is monitored intermittently, periodically, or throughout the course of a therapeutic treatment. In some embodiments, the MIC value is monitored intermittently, periodically, or throughout the course of a therapeutic treatment. In some embodiments, if the MIC value has increased during the course of therapy, it is indicative that the bacterium is likely to develop resistance.

In some embodiments, resistance is monitored during the course of treatment with vancomycin. In some embodiments, susceptibility testing such as Kirby-Bauer method (disk diffusion method), Stokes method, Epsilometer test, agar dilution, broth dilution, or a combination thereof, is used to monitor the development of resistance to vancomycin. In some embodiments, resistance is monitored intermittently, periodically, or throughout the course of vancomycin therapy. In some embodiments, if the MIC value has increased during the course of vancomycin therapy, it is indicative that the bacterium has most likely developed resistance to vancomycin.

Topical Ointment Formulation

Disclosed herein are methods and formulations for topical administration in the treatment of skin conditions or diseases. In some embodiments, the active ingredient is vancomycin hydrochloride. Vancomycin is a glycopeptides antibiotic used as a penicillin alternative. In some cases, the rise of penicillin-resistant strains of bacteria such as MRSA and MRSE has induced vancomycin as a first-line therapy. In some embodiments, the composition comprising vancomycin hydrochloride is formulated as a lotion, cream, ointment, foam, paste or gel or any other physical form known for topical administration. In some embodiment, the composition comprising vancomycin hydrochloride is formulated as an ointment. U.S. Pat. No. 6,852,311 discloses ointment formulations for use for the composition disclosed herein, which is incorporated by reference in its entirety.

In some embodiments, the composition comprising vancomycin hydrochloride further comprises an ointment base. In some embodiments, the base includes, but is not limited to, liquid paraffin, white petrolatum, waxes, esters of fatty alcohols, saturated fatty acids, oleic acid, olive oil, starch glycerin, purified lanolin, cetyl alcohol, glyceryl monostearate, methylparaben, propylparaben, glycol ethers, gelation hydrocarbon, polyethylene glycol, polyoxyl 40 stearate, polysorbates, hydrophilic ointment base, white ointment base, absorptive ointment base, Macrogol ointment base, simple ointment base, and the like. In some embodiments, the base includes liquid paraffin, white petrolatum, purified lanolin, gelation hydrocarbon, polyethylene glycol, hydrophilic ointment base, white ointment base, absorptive ointment base, Macrogol ointment base, simple ointment base, and the like. In some embodiments, the base includes liquid paraffin, white petrolatum, purified lanolin, gelation hydrocarbon, a polyethylene glycol, hydrophilic ointment base, white ointment base, simple ointment base, and mixtures thereof.

In some embodiments, the topical ointment further contains excipients in a range without affecting the intended functions and stability of the vancomycin hydrochloride to be contained. Exemplary excipients include, but are not limited to, antiseptics such as parahydroxybenzoate, chlorobutanol, benzalkonium chloride and the like; surfactants such as polysorbate 80, polyoxyl 40 stearate, polyoxyethylene hydrogenated castor oil and the like; stabilizers such as sodium edetate, citric acid, and salts thereof; alcohols such as glycerol, lanolin alcohol, cetanol and the like; esters such as isopropyl myristate, ethyl linoleate and the like; and oils such as olive oil and triglycerides of middle-chained fatty acids. In some embodiments, the excipient includes antiseptics, surfactants, stabilizers, alcohols, esters, oils, and mixtures thereof.

In some embodiments, the topical ointment formulation comprises additional ingredients such as penetration enhancer, oil, waxy compound, surfactant, stabilizer, gelling agent, moisturizer, water or a preservative.

In some embodiments, penetration enhancers serve to improve the absorption across the skin of the composition comprising vancomycin hydrochloride. Penetration enhancers include vitamin E TPGS (Eastman Chemical Company, Kingsport, Tenn.), and other vitamin E derivatives as described in U.S. Pat. No. 6,193,985; and glyceryl monocaprylate/caprate (Cornwell et al. 1998, Int. J. Pharmaceutics, 171(2): 243-255). In some embodiments, additional penetration enhancers are described in Smith and Maibach (eds.), *Percutaneous Penetration Enhancers*, CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, I. L. (1997).

In some embodiments, the oils, waxy compounds, gelling agents and surfactants selected for the formulation and stabilization of the compositions comprising vancomycin hydrochloride are those traditionally employed in the dermatological arts. In some embodiments, the optional oils and/or waxy compounds constitute from 0.5% to 99.9% of the total weight of the composition. The amount of oil and/or wax depends on the actual form or physical state of the composition. Exemplary of such oils are mineral oils (petrolatum); vegetable oils (sweet almond, macadamia, blackcurrant-pip oil); synthetic oils such as perhydrosqualene, fatty alcohols, acids or esters (octyl palmitate, isopropyl lanolate, triglycerides including those of capric/caprylic acids), oxyethylenated or oxypropylenated fatty esters and ethers; and silicone oils (cyclomethicone, polydimethylsiloxanes or PDMS) or fluorinated oils. Exemplary waxy compounds include jojoba oil, paraffin, carnauba wax and beeswax.

Exemplary surfactants (emulsifying and coemulsifying) include the esters of fatty acids and polyethylene glycol (PEG), esters of fatty acids and glycerol (glyceryl stearate) or esters of fatty acids and sugar (sorbitan stearate), as well as the polyoxyethylenated or polyoxypropylenated derivatives thereof, cyclomethicones and dimethicone copolyols, and also anionic surfactants (K or Na alkyl phosphate).

Exemplary stabilizer includes glycol stearate or PEG-150 distearate. The stabilizer, when used, is typically present in an amount from about 0.1 to 5 weight percent of the composition.

Exemplary gelling agents include modified clays (bentones), metal salts of fatty acids (aluminum stearate), ethylene/acrylate copolymers, silicas, polyethylenes, calcium silicates or, alternatively, ethyl cellulose.

Exemplary moisturizers include wheat protein (e.g., laurdimonium hydroxypropyl hydrolyzed wheat protein), hair keratin amino acids, sodium peroxylinecarbolic acid, panthenol, tocopherol (Vitamin E), dimethicone, and the like, and mixtures thereof. Sodium chloride may also be present, particularly when hair keratin amino acids are included as a moisturizer. Moisturizers, when used, are typically present in an amount from about 0.01 to 2 weight percent, preferably about 0.05 to 1.5 weight percent, more preferably from about 0.1 to 1 weight percent of the composition.

In some embodiments, water used is deionized water.

Exemplary preservatives include tetrasodium ethylene-diamine tetraacetic acid (EDTA), methylparaben, benzophenone-4, methylchloroisothiazolinone, methylisothiazolinone, and the like, and mixtures thereof. Preservatives, when used, are typically present in an amount from about 0.01 to 6 weight percent.

In some embodiments, the topical ointment are formulated as follows: antiseptics, surfactants, stabilizers, alcohols, esters or oils are blended with an ointment base such as liquid paraffin or white petrolatum placed in a mortar or a mixing machine for ointment to form a mixture. In some embodiments, this is followed by addition of vancomycin hydrochloride, and the resulting mixture is mixed until uniform and kneaded to form the ointment.

In some embodiments, the topical ointment comprises about 0.01% to about 10% of vancomycin hydrochloride. In some embodiments, the topical ointment comprises about 0.05% to about 9%, about 0.1% to about 8%, about 0.5% to about 7%, or about 1% to about 5% of vancomycin hydrochloride. In some embodiments, the topical ointment comprises about 0.01%, about 0.05%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, or about 10% of vancomycin hydrochloride.

In some embodiments, the topical ointment is administrated to a mammal, (e.g. human or non-human mammals). In some embodiments, the topical ointment is applied to the skin, or to other epithelia such as the nares, scalp, ears, vagina and oral cavity. As disclosed elsewhere herein, the topical ointment is administered to treat skin infections associated with, caused by, or complicated by Gram positive bacteria. In some embodiments, the skin infections is associated with, caused by, or complicated by *Staphylococcus aureus, Staphylococcus epidermidis*, methicillin-resistant *Staphylococcus aureus* (MRSA), methicillin-resistant *Staphylococcus epidermidis* (MRSE), *Steptococcus pyogenes*, and *Steptococcus agalactiae*. In some embodiments, the skin infections is associated with, caused by, or complicated by methicillin-resistant *Staphylococcus aureus* (MRSA). In some embodiments, the skin infections is associated with, caused by, or complicated by methicillin-resistant *Staphylococcus epidermidis* (MRSE).

Particle Size

Size reduction is used to increase surface area, modulate formulation delivery properties, and/or improve stability. It is also used to maintain a consistent average particle size distribution (PSD) (e.g., micrometer-sized particles, nanometer-sized particles or the like) for any formulation described herein. In some embodiments, any formulation described herein comprises mulitparticulats, i.e., a plurality of particle sizes (e.g., micronized particles, nano-sized particles, non-sized particles, colloidal particles) to form a multiparticulate formulation. In some embodiments, any formulation described herein comprises one or more multiparticulate vancomycin hydrochloride. In some embodiments, any composition described herein comprises micronized particles of vancomycin hydrochloride. In some embodiments, any formulation described herein comprises vancomycin hydrochloride that is essentially in the form of micronized particles. In some embodiments, any formulation described herein comprises vancomycin hydrochloride that is in the form of micronized particles. Micronization is a process of reducing the average diameter of particles of a solid material. Micronized particles are micrometer-sized in diameter. In some embodiments, the average diameter of particles in a micronized solid is from about 1 μm to about 500 μm. In some embodiments, the average diameter of particles in a micronized solid is from about 1 μm to about 200 μm. In some embodiments, the average diameter of particles in a micronized solid is from about 2 μm to about 100 μm. In some embodiments, the average diameter of particles in a micronized solid is from about 3 μm to about 50 μm. In some embodiments, a particulate micronized solid comprises particle sizes of less than about 5 microns, less than about 20 microns and/or less than about 100 microns. In some embodiments, the use of micronized particles of vancomycin hydrochloride in the ointment formulation allows for improved tunable and/or controllable delivery of vancomycin hydrochloride into desirable depth of the skin compared to a similar ointment formulation of comprising non-micronized vancomycin hydrochloride.

In some embodiments, the micronized vancomycin hydrochloride has an average particle size of from about 1 μm to about 100 μm. In some embodiments, the micronized vancomycin hydrochloride has an average particle size of from about 1 μm to about 90 μm. In some embodiments, the micronized vancomycin hydrochloride has an average particle size of from about 1 μm to about 80 μm. In some embodiments, the micronized vancomycin hydrochloride has an average particle size of from about 1 μm to about 75 μm. In some embodiments, the micronized vancomycin hydrochloride has an average particle size of from about 5 μm to about 75 μm. In some embodiments, the micronized vancomycin hydrochloride has an average particle size of from about 10 μm to about 75 μm. In some embodiments, the micronized vancomycin hydrochloride has an average particle size of from about 10 μm to about 60 μm. In some embodiments, the micronized vancomycin hydrochloride has an average particle size of from about 10 μm to about 50 μm. In some embodiments, the micronized vancomycin hydrochloride has an average particle size of from about 10 μm to about 40 μm. In some embodiments, the micronized vancomycin hydrochloride has an average particle size of from about 20 μm to about 30 μm.

Particle size reduction techniques include, by way of example, grinding, milling (e.g., air-attrition milling (jet milling), ball milling), coacervation, complex coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments formulations described herein comprise crystalline particles and/or isotropic particles. In some embodiments, formulations described herein comprise amorphous particles and/or anisotropic particles.

In specific embodiments, any skin ointment composition described herein comprises micronized vancomycin hydrochloride. In some of such embodiments, micronized vancomycin hydrochloride comprises micronized particles. In some of such embodiments, a micronized vancomycin hydrochloride comprising micronized particles of vancomycin hydrochloride without any coating or encapsulation. In certain embodiments, the skin ointment composition described herein comprises vancomycin hydrochloride as a micronized powder.

Dosing and Treatment Regiments

Disclosed herein, in some embodiments, are compositions for topical administration comprising the active ingredient vancomycin hydrochloride. In some embodiments, the topical ointment comprises about 0.01% to about 10% of vancomycin hydrochloride. In some embodiments, the topical ointment comprises about 0.1% to about 8% of vancomycin hydrochloride. In some embodiments, the topical ointment comprises about 1% to about 5% of vancomycin hydrochloride.

In some embodiments, the topical ointment penetrates through the skin layers. In some embodiments, the skin comprises an epidermis layer, a dermis layer, and a subcutaneous tissue layer. In some embodiments, the topical ointment penetrates into the epidermis layer. In some embodiments, the topical ointment penetrates into the dermis layer. In some embodiments, the topical ointment penetrates into the subcutaneous tissue layer. In some embodiments, the topical ointment penetrates into the muscle.

In some embodiments, the topical ointment penetrates through the skin at a depth from about 0.05 mm to about 20 mm. In some embodiments, the topical ointment penetrates through the skin at a depth from about 0.1 mm to about 18 mm, about 0.3 mm to about 15 mm, about 0.5 mm to about 13 mm, about 1 mm to about 10 mm, or about 3 mm to about 6 mm. In some embodiments, the topical ointment penetrates through the skin at a depth of about 0.1 mm, about 0.2 mm, about 0.4 mm, about 0.6 mm, about 0.8 mm, about 1 mm, about 1.2 mm, about 1.4 mm, about 1.6 mm, about 1.8 mm, about 2 mm, about 2.2 mm, about 2.4 mm, about 2.8 mm, about 3 mm, about 3.2 mm, about 3.4 mm, about 3.6 mm, about 3.8 mm, about 4 mm, about 4.2 mm, about 4.4 mm, about 4.6 mm, about 4.8 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 10.5 mm, about 11 mm, about 12 mm, about 13 mm, about 14 mm, about 15 mm, about 16 mm, about 17 mm, about 18 mm, about 19 mm, or about 20 mm.

In some embodiments, the topical ointment penetrates into the epidermis layer at a concentration of that is higher than the minimum inhibitory concentration (MIC) of the target tissue. In some embodiments, MIC is a method for quantitatively assessing the antimicrobial activity of the compound in a target organism or target tissue. In some embodiments, the topical ointment penetrates into the epidermis layer at a concentration of at least 6 times to at least 20 times higher than the MIC of the target tissue layer. In some embodiments, the topical ointment penetrates into the epidermis layer at a concentration of at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, or at least 20 times higher than the MIC of the target tissue layer. In some embodiments, the topical ointment penetrates into the epidermis layer at a concentration of at least 10 times, at least 11 times, or at least 12 times higher than the MIC of the target tissue layer. In some embodiments, the topical ointment penetrates into the epidermis layer at a concentration of at least 10 times higher than the MIC of the target tissue layer. In some embodiments, the topical ointment penetrates into the epidermis layer at a concentration of at least 11 times higher than the MIC of the target tissue layer. In some embodiments, the topical ointment penetrates into the epidermis layer at a concentration of at least 12 times higher than the MIC of the target tissue layer.

In some embodiments, the topical ointment penetrates into the dermis layer at a concentration of that is higher than the minimum inhibitory concentration (MIC) of the target tissue. In some embodiments, the topical ointment penetrates into the dermis layer at a concentration of at least 6 times to at least 20 times higher than the MIC of the target tissue layer. In some embodiments, the topical ointment penetrates into the dermis layer at a concentration of at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, or at least 20 times higher than the MIC of the target tissue layer. In some embodiments, the topical ointment penetrates into the dermis layer at a concentration of at least 10 times, at least 11 times, or at least 12 times higher than the MIC of the target tissue layer. In some embodiments, the topical ointment penetrates into the dermis layer at a concentration of at least 10 times higher than the MIC of the target tissue layer. In some embodiments, the topical ointment penetrates into the dermis layer at a concentration of at least 11 times higher than the MIC of the target tissue layer. In some embodiments, the topical ointment penetrates into the dermis layer at a concentration of at least 12 times higher than the MIC of the target tissue layer.

In some embodiments, the topical ointment penetrates into the subcutaneous tissue layer at a concentration of that is higher than the minimum inhibitory concentration (MIC) of the target tissue. In some embodiments, the topical ointment penetrates into the subcutaneous tissue layer at a concentration of at least 6 times to at least 20 times higher than the MIC of the target tissue layer. In some embodiments, the topical ointment penetrates into the subcutaneous tissue layer at a concentration of at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, or at least 20 times higher than the MIC of the target tissue layer. In some embodiments, the topical ointment penetrates into the subcutaneous tissue layer at a concentration of at least 10 times, at least 11 times, or at least 12 times higher than the MIC of the target tissue layer. In some embodiments, the topical ointment penetrates into the subcutaneous tissue layer at a concentration of at least 10 times higher than the MIC of the target tissue layer. In some embodiments, the topical ointment penetrates into the subcutaneous tissue layer at a concentration of at least 11 times higher than the MIC of the target tissue layer. In some embodiments, the topical ointment penetrates into the subcutaneous tissue layer at a concentration of at least 12 times higher than the MIC of the target tissue layer.

In some embodiments, the topical ointment penetrates into the muscle at a concentration of that is higher than the MIC of the target muscle. In some embodiments, the topical ointment penetrates into the muscle at a concentration of at least 6 times to at least 20 times higher than the MIC of the target muscle. In some embodiments, the topical ointment penetrates into the muscle at a concentration of at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, or at least 20 times higher than the MIC of the target muscle. In some embodiments, the topical ointment penetrates into the muscle at a concentration of at least 10 times, at least 11 times, or at least 12 times higher than the MIC of the target muscle. In some embodiments, the topical ointment penetrates into the muscle at a concentration of at least 10 times higher than the MIC of the target muscle. In some embodiments, the topical ointment penetrates into the muscle at a concentration of at least 11 times higher than the MIC of the target muscle. In some embodiments, the topical ointment penetrates into the muscle at a concentration of at least 12 times higher than the MIC of the target muscle.

In some embodiments, the topical ointment is administered once per day, twice per day, three times per day, four times per day, five times per day or more frequent, everyday, once per week, twice per week, three times per week, four times per week, five times per week, six times per week, every other day, every other week, once per month, twice per month, three times per month, continuously over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or more. In some embodiments, the topical ointment is administered once per day.

In some embodiments, the topical ointment is administered in combination with a second therapeutic agent. In some embodiments, the topical ointment in combination with the second therapeutic agent is administered once per day, twice per day, three times per day, four times per day, five times per day or more frequent, everyday, once per week, twice per week, three times per week, four times per week, five times per week, six times per week, every other day, every other week, once per month, twice per month, three times per month, continuously over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or more. In some embodiments, the topical ointment in combination with the second therapeutic agent is administered once per day. In some embodiments, the second therapeutic agent is administered before, during or after the administration of the topical ointment. In some embodiments, the topical ointment and the second therapeutic agent are administered simultaneously, sequentially, or intermittently.

Exemplary therapeutic agents include, but are not limited to, vancomycin intravenous; rifampin; gentamicin; β-lactam such as cephalosporins (e.g., cefadroxil, cefazolin, cefalexin, cefaclor, cefprozil, cefuroxime, cefixime, cefdinir, cefditoren, cefotaxime, cefpodoxime, ceftazidime, ceftibuten, ceftriaxone, cefepime, cefpirome, ceftaroline fasamil, ceftobiprole), carbapenems (e.g. doripenem, ertapenem, imipenem, cilastatin and meropenem), panipenem, ceftobiprole, or nafcillin; lincosamides (e.g. clindamycin, lincomycin); lipopeptide (e.g. daptomycin); oxazolidonones (e.g. linezolid); macrolides (e.g. azithromycin, clarithromycin, dirithromycin, erythromycin, roxithromycin); chloramphenicol; quinupristin-dalfopristin; or a combination thereof.

In some embodiments, the second therapeutic agent include vancomycin intravenous, rifampin, gentamicin, cefadroxil, cefazolin, cefalexin, cefaclor, cefprozil, cefuroxime, cefixime, cefdinir, cefditoren, cefotaxime, cefpodoxime, ceftazidime, ceftibuten, ceftriaxone, cefepime, cefpirome, ceftaroline fasamil, ceftobiprole, doripenem, ertapenem, imipenem, cilastatin, meropenem, panipenem, ceftobiprole, nafcillin, clindamycin, lincomycin, daptomycin, linezolid, azithromycin, clarithromycin, dirithromycin, erythromycin, roxithromycin, chloramphenicol, quinupristin-dalfopristin, or a combination thereof. In some embodiments, the second therapeutic agent is vancomycin intravenous.

In some embodiments, the topical ointment comprising vancomycin is administered to treat a patient having a skin condition caused by a bacterial infection. In some embodiments, the topical ointment comprising vancomycin is administered to a patient to reduce the progression of a skin condition caused by a bacterial infection, reverse the progression of a skin condition caused by a bacterial infection, or eliminate a skin condition caused by a bacterial infection in the patient.

In some embodiments, wherein the patient's status does improve, upon the doctor's discretion the administration of the topical ointment may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

In some embodiments, the emergence of resistance is monitored during the course of the therapeutic treatment. In some embodiments, resistance is monitored using a susceptibility testing. In some embodiments, resistance is monitored intermittently, periodically, or throughout the course of treatment. In some embodiments, the therapeutic treatment is discontinued when the bacteria has developed resistance to vancomycin. In some embodiments, the therapeutic treatment is continued when the bacteria remains susceptible to vancomycin.

As disclosed herein, the terms "patient(s)", "subject(s)" and "individual(s)", mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

Analytical Techniques and Instrumentations

Sample Preparation

Methods described herein are compatible with a variety of sample preparation techniques well known in the art. In some embodiments, a sample refers to a biological sample such as a blood, urine, bone, tissue (e.g. muscle), sputum, saliva, or skin sample. In some embodiments, a sample is collected from a site of infection. In some embodiments, a sample is a blood, tissue (e.g. muscle) or skin sample. In some embodiments, the sample is a blood sample. In some embodiments, the sample is a tissue (e.g. muscle) sample. In some embodiments, a sample is a skin sample. In some embodiments, a skin sample is collected form a site of infection. In some embodiments, the skin comprises an epidermis layer, a dermis layer, and a subcutaneous tissue layer. In some embodiments, the skin sample is an epidermis skin sample, a dermis skin sample, or a subcutaneous tissue sample. In some embodiments, the site of infection leads to one or more skin conditions such as impetigo, ecthyma, Staphylococcal scalded skin syndrome (SSSS), erysipelas, cellulitis, abscess, necrotizing fasciitis, folliculitis, furunculosis, carbunculosis, or secondary skin infection. In some embodiments, the infection is caused by, or complicated by a Gram positive bacteria, for example, such as but not limiting to *Staphylococcus aureus, Staphylococcus epidermidis*, methicillin-resistant

*Staphylococcus aureus* (MRSA), methicillin-resistant *Staphylococcus epidermidis* (MRSE), *Streptococcus pyogenes*, and *Streptococcus agalactiae*.

In some embodiments, the sample is a skin sample. In some embodiments, the skin samples are washed, homogenized, centrifuged, sonicated, and filtered using a solid phase extraction column prior to proceeding to an analytical step. In some embodiments, the blood sample is extracted using a solid phase extraction column prior to proceeding to an analytical step. The following sample preparation techniques are for illustrative purposes only and should not be construed as limiting in any manner.

In some embodiments, the skin samples are rinsed with saline and then pressed in sterile gauze to remove contaminating blood, and are subsequently weighed. In some embodiments, the samples are assayed against a calibration curve of vancomycin in water. Water (500 µl) is added to the tissue samples which are then homogenized. In some embodiments, an additional 500 µl water are added in order to remove all sample traces from the homogenizer. The mixture is then centrifuged to avoid loss of material on the tube walls, followed by sonication in an ice bath for 20 min. Internal standard (IS) containing tinisazole (20 µg ml$^{-1}$ in H$_2$O) (200 µl) is then added to this mixture. In some embodiments, a sample of the upper layer (500 µl) is applied to the SPE (C18 Bond Elut) cartridge. The cartridges have been activated prior to use by successive washing with 3 ml methanol and 3 ml distilled water.

In some embodiments, after centrifugation for 1 min at 250 rpm, the cartridge is washed with 1.5 ml H$_2$O. The eluate is discarded and the cartridge was washed again with a 3 ml methanol-water mixture (5:95 v:v). In some embodiments, vancomycin and the IS are eluted by two successive 300 ml washing with acetonitrile-50 mM KH$_2$PO$_4$ (50:50 v:v, pH_4.0, 1 min centrifugation at 250 rpm), and the eluate is evaporated to dryness, and then reconstituted with 600 ml water. This solution (100 ml) is used for the analytical step.

In some embodiments, the SPE cartridges are washed with one volume of methanol followed by one volume of water. Each cartridge is discarded after the second run.

In some embodiments, the sample is a blood sample. In some embodiments, to a 0.5 mL spiked blood or plasma, a 100 ml IS solution (20 µg ml$^{-1}$ in H$_2$O) is added. This mixture (250 µl) is then applied to a Bond Elut C18 cartridge. The cartridges have already been activated prior to use by successive washing with 3 ml methanol and 3 ml distilled water. After centrifugation for 1 min at 250 rpm, the cartridge is washed with 1.5 ml H$_2$O. The eluate is discarded and the cartridge is washed again with a 3 ml methanol-water mixture (5:95 v:v). Vancomycin and the IS are eluted by two successive 300 µl washing with acetonitrile-50 mM KH$_2$PO$_4$ (50:50 v:v; pH at 4.0; 1 min centrifugation at 250 rpm), and the eluate is evaporated to dryness, and then reconstituted with 600 µl water. This solution (100 µL) is then used for the analytical step.

Sample Analysis

Methods described herein are compatible with a variety of analytical techniques well known in the art, including liquid chromatography (LC) (e.g. high performance liquid chromatography), liquid chromatography-mass spectrometry (LC-MS), gas chromatography-mass spectrometry (GC-MS), capillary electrophoresis-mass spectrometry (CE-MS), and nuclear magnetic resonance imaging (NMR). In some embodiments, a LC method (e.g. high performance liquid chromatography) is used. In some embodiments, the sample processed is a tissue sample. In some embodiments, the tissue sample is processed by a LC method. In some embodiments, the tissue sample is processed by a LC method in combination with a second method.

In some embodiments, the LC method is any suitable LC methods well known in the art, for separation of a sample into its individual parts. This separation occurs based on the interaction of the sample with the mobile and stationary phases. Since there are many stationary/mobile phase combinations that are employed when separating a mixture, there are several different types of chromatography that are classified based on the physical states of those phases. In some embodiments, the LC is further classified as normal-phase chromatography, reverse-phase chromatography, size-exclusion chromatography, ion-exchange chromatography, affinity chromatography, displacement chromatography, partition chromatography, flash chromatography, chiral chromatography, and aqueous normal-phase chromatography.

In some embodiments, the LC method is a high performance liquid chromatography (HPLC) method. In some embodiments, the HPLC method is further categorized as normal-phase chromatography, reverse-phase chromatography, size-exclusion chromatography, ion-exchange chromatography, affinity chromatography, displacement chromatography, partition chromatography, chiral chromatography, and aqueous normal-phase chromatography.

In some embodiments, the HPLC method of the present disclosure is performed by any standard techniques well known in the art. Exemplary HPLC methods include hydrophilic interaction liquid chromatography (HILIC), electrostatic repulsion-hydrophilic interaction liquid chromatography (ERLIC) and reverse phase liquid chromatography (RPLC). The following HPLC methods are for illustrative purposes only and should not be construed as limiting in any manner.

In some embodiments, the HPLC system consisted of a gradient system model HP-1050 with a UV-vis detector and an autosampler (Hewlett-Packard). Chromatographic separations are performed at ambient temperature (23-25° C.) on a Hypersil BDS C8 column; 10 cm×4.6 mm, 3 µm (Shandon) with a C8 2 cm guard column (Keystone Scientific). The mobile phase consisted of 5 mM potassium dihydrogen phosphate buffer (pH 2.8)-acetonitrile, and the following gradient is applied: 3% acetonitrile for 1.5 min; 20% at 11.5 min, 20% at 14 min and 3% at 15 min; post time is 10 min. The total run time is 25 min at a flow rate of 1.5 ml min$^{-1}$. In some embodiments, detection of vancomycin and IS are at 282 nm. In some embodiments, fluorescence polarization immunoassay (FPIA) is performed on a TDX system (Abbott Laboratories).

In some embodiments, calibration curves of vancomycin are established to validate the HPLC method. In some embodiments, fifteen calibration curves of vancomycin, within a concentration range of 0.5-75 µg ml$^{-1}$ in plasma and 0.25-20 µg ml$^{-1}$ in water, are run in order to establish linearity. In some embodiments, the calibration curves are obtained by weighted (1/X$^2$) linear regression of the peak height of vancomycin versus vancomycin concentration. Recovery is calculated by comparing the measured values of the spiked samples with those of the standard aqueous solutions of three concentrations, namely, 2, 10 and 40 µg ml$^{-1}$. The extraction recovery of the IS is determined at 5 µg ml$^{-1}$. In some embodiments, the stability is established with six replicates of the three above mentioned concentrations, as follows: stability on the autosampler during 24 h, long term stability up to 6 months at −36° C., and stability to two freeze-thaw cycles of the samples. In some embodiments, inter-day reproducibility is measured at three time points and the coefficients of variation are 7.5, 6.0 and 6.4% for 2, 10 and 40 µg ml$^{-1}$, respectively. The intra-day coefficients of variation, measured for eight replicates of each of the above mentioned concentrations, are 11.2, 8.5 and 8.6%, respectively.

In some embodiments, the LC is coupled to a mass spectroscopy as a LC-MS method. In some embodiments, the LC-MS method includes ultra-performance liquid chromatography-electrospray ionization quadrupole time-of-flight mass spectrometry (UPLC-ESI-QTOF-MS), ultra-performance liquid chromatography-electrospray ionization tandem mass spectrometry (UPLC-ESI-MS/MS), reverse phase liquid chromatography-mass spectrometry (RPLC-MS), hydrophilic interaction liquid chromatography-mass spectrometry (HILIC-MS), hydrophilic interaction liquid chromatography-triple quadrupole tandem mass spectrometry (HILIC-QQQ), electrostatic repulsion-hydrophilic interaction liquid chromatography-mass spectrometry (ERLIC-MS), liquid chromatography time-of-flight mass spectrometry (LC-QTOF-MS) and liquid chromatography-tandem mass spectrometry (LC-MS/MS). In some embodiments, the LC-MS method of the present disclosure is performed by standard techniques well known in the art.

In some embodiments, the GC is coupled to a mass spectroscopy as a GC-MS method. In some embodiments, the GC-MS method includes two-dimensional gas chromatography time-of-flight mass spectrometry (GC*GC-TOFMS), gas chromatography time-of-flight mass spectrometry (GC-QTOF-MS) and gas chromatography-tandem mass spectrometry (GC-MS/MS).

In some embodiments, CE is coupled to a mass spectroscopy as a CE-MS method. In some embodiments, the CE-MS method includes capillary electrophoresis-negative electrospray ionization-mass spectrometry (CE-ESI-MS), capillary electrophoresis-negative electrospray ionization-quadrupole time of flight-mass spectrometry (CE-ESI-QTOF-MS) and capillary electrophoresis-quadrupole time of flight-mass spectrometry (CE-QTOF-MS).

In some embodiments, the nuclear magnetic resonance (NMR) method is any suitable method well known in the art for the detection of one or more metabolites disclosed herein. In some embodiments, the NMR method includes one dimensional (1D) NMR methods, two dimensional (2D) NMR methods, solid state NMR methods and NMR chromatography. Exemplary 1D NMR methods include $^1$Hydrogen, $^{13}$Carbon, $^{15}$Nitrogen, $^{17}$Oxygen, $^{19}$Fluorine, $^{31}$Phosphorus, $^{39}$Potassium, $^{23}$Sodium, $^{33}$Sulfur, $^{87}$Strontium, $^{27}$Aluminium, $^{43}$Calcium, $^{35}$Chlorine, $^{37}$Chlorine, $^{63}$Copper, $^{65}$Copper, $^{57}$Iron, $^{25}$Magnesium, $^{199}$Mercury or $^{67}$Zinc NMR method, distortionless enhancement by polarization transfer (DEPT) method, attached proton test (APT) method and 1D-incredible natural abundance double quantum transition experiment (INADEQUATE) method. Exemplary 2D NMR methods include correlation spectroscopy (COSY), total correlation spectroscopy (TOCSY), 2D-INADEQUATE, 2D-adequate double quantum transfer experiment (ADEQUATE), nuclear overhauser effect spectroscopy (NOSEY), rotating-frame NOE spectroscopy (ROESY), heteronuclear multiple-quantum correlation spectroscopy (HMQC), heteronuclear single quantum coherence spectroscopy (HSQC), short range coupling and long range coupling methods. Exemplary solid state NMR method include solid state $^{13}$Carbon NMR, high resolution magic angle spinning (HR-MAS) and cross polarization magic angle spinning (CP-MAS) NMR methods. Exemplary NMR chromatography include diffusion ordered spectroscopy (DOSY), DOSY-TOCSY and DOSY-HSQC.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include topical ointment comprising vancomycin hydrochloride, optionally in combination with vancomycin intravenous as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

These examples are provided for illustrative purposes only and not to limit the scope of the claims provided herein.

Example 1

15 g of liquid paraffin and 84.99 g of white petrolatum are placed in a mortar and are mixed and kneaded until uniform. This is followed by addition of 0.01 g of micronized vancomycin hydrochloride and the resulting mixture is thoroughly kneaded to form a homogenous topical ointment containing 0.01% of vancomycin hydrochloride.

Example 2

15 g of liquid paraffin and 83.9 g of white petrolatum are placed in a mortar and are mixed and kneaded until uniform.

This is followed by addition of 1.1 g of micronized vancomycin hydrochloride and the resulting mixture is thoroughly kneaded to form a homogenous topical ointment containing 1.1% of vancomycin hydrochloride.

Example 3

15 g of liquid paraffin and 80 g of white petrolatum are placed in a mortar and are mixed and kneaded until uniform. This is followed by addition of 5 g of micronized vancomycin hydrochloride and the resulting mixture is thoroughly kneaded to form a homogenous topical ointment containing 5% of vancomycin hydrochloride.

Example 4

15 g of liquid paraffin and 75 g of white petrolatum are placed in a mortar and are mixed and kneaded until uniform. This is followed by addition of 10 g of micronized vancomycin hydrochloride and the resulting mixture is thoroughly kneaded to form a homogenous topical ointment containing 10% of vancomycin hydrochloride.

Example 5

The storage stability of the topical ointments containing micronized vancomycin hydrochloride obtained in Examples 1-4 is tested.
Each of the skin ointments is filled in a plastic tube and is stored in a thermostatic bath kept either at 25° C. or at 30° C. High-performance liquid chromatography (HPLC) is used to determine the remaining ratio of vancomycin hydrochloride as a measurement against time. The topical ointments are tested at 1 month or 2 months intervals.

Example 6

The tissue concentrations of topical vancomycin ointment were compared as a single dose to a single dose of vancomycin intravenous (IV). In this experiment, 48 hairless guinea pigs in 6 groups of 8 guinea pigs each were dosed with either a weight appropriate vancomycin IV dose, a 1.1% ointment formulation referred to as a low topical dose, or a 5% ointment formulation referred to as a high topical dose.

The guinea pigs were further divided into animals with intact skin and animals with abraded skin. Animals were sacrificed at time intervals of 1, 2, 4, and 24 hours, and the tissues were frozen prior to evaluation.

An HPLC method was employed to measure vancomycin (topical) levels and vancomycin IV levels in the epidermis layer, the dermis layer, muscle at the dose site, muscle at 1 inch away from the dose site, and in the blood.

Effect of Vancomycin in the Plasma

The concentration of vancomycin (topical) in the plasma was calculated to be lower than 50 ng/mL across all animal groups, e.g. receiving either a low topical dose or a high topical dose, and having non-abraded skin and abraded skin groups (FIG. 3). In some cases and without wishing to be bound by any particular theory, this observation would indicated that a low concentration of vancomycin (topical) penetrated into the plasma. Furthermore, a peak was not observed in the 1 h, 2 h, 4 h, or 24 h time points.

Effect of Vancomycin in Animals with Non-Abraded Skin

Figure 4:
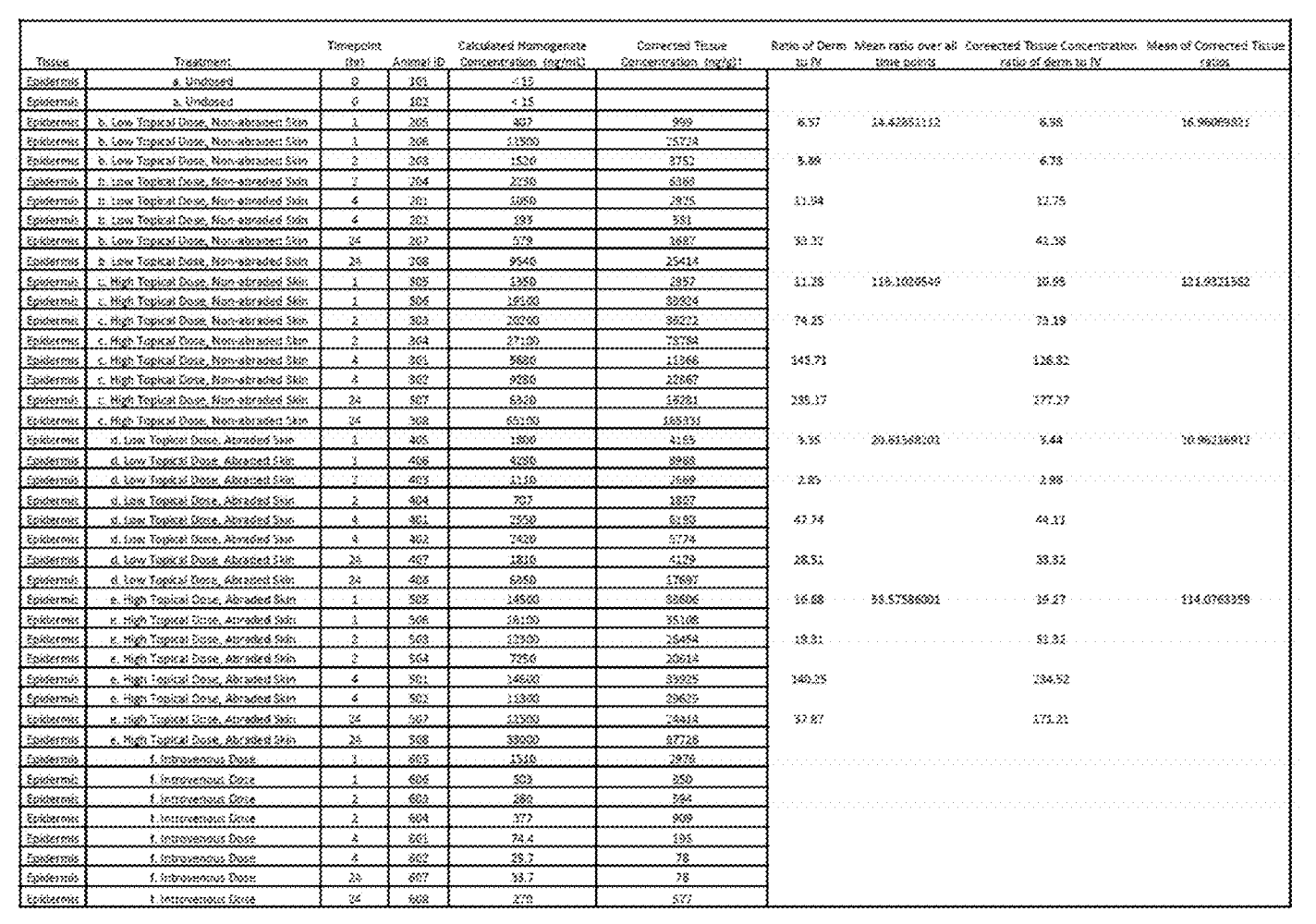
Figure 6:
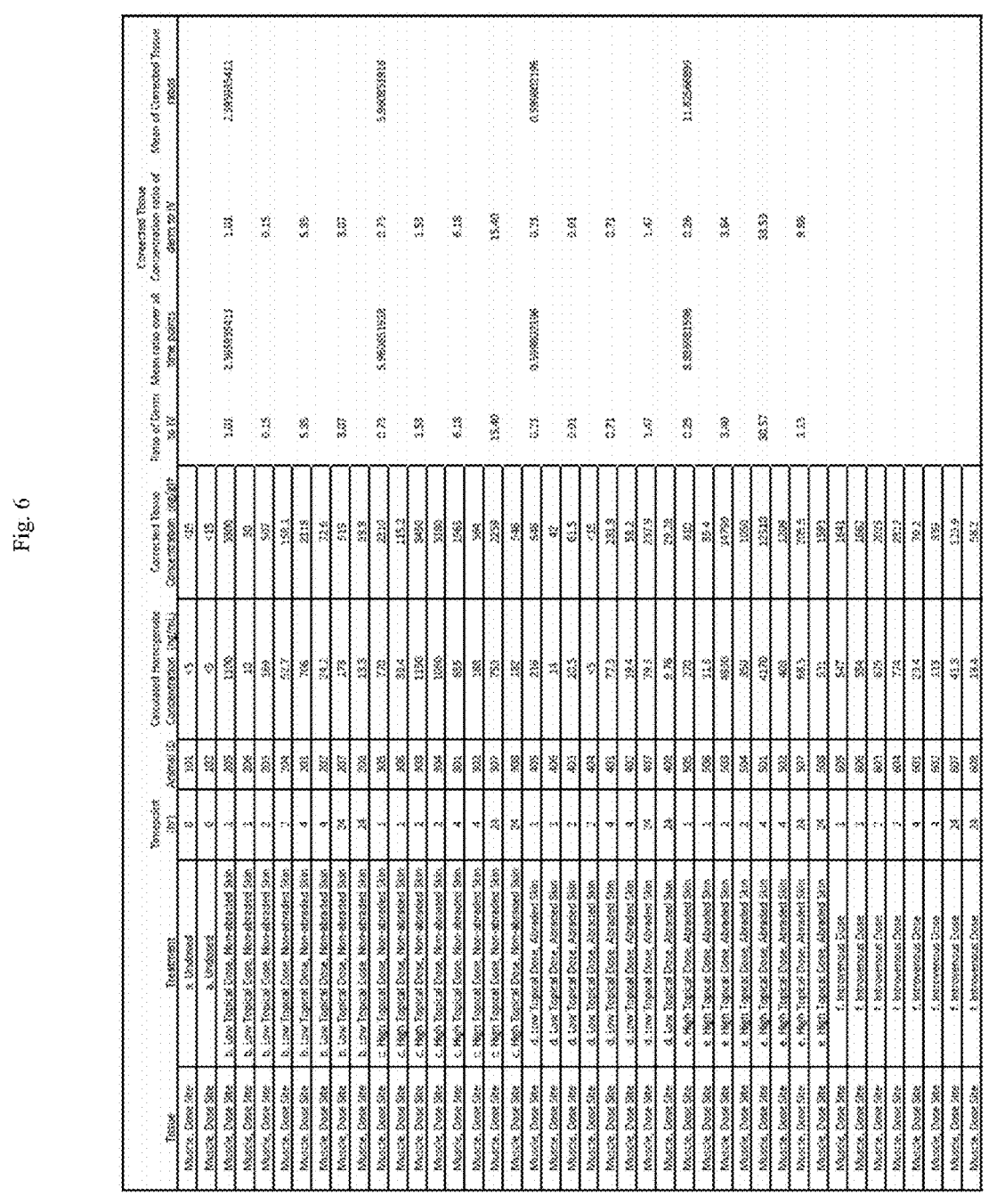

In animals with non-abraded skin, a higher amount of vancomycin (topical) was observed in the epidermis layer (FIG. 4) than in the dermis layer (FIG. 5). Low levels of vancomycin (topical) were observed in both the muscle at dose site (FIG. 6), and the muscle 1 inch away from dose site (FIG. 7). At the epidermis layer, animals receiving a high topical dose exhibited a higher concentration than animals receiving a low topical dose. In addition, both subgroups, low topical dose and high topical dose, reached a peak concentration at 24 hours. A similar trend was observed at the dermis layer. In both the low topical dose and high topical dose subgroups, a peak concentration was observed at 24 hours. In muscle at dose site, a peak was observed at 4 hours in the low topical dose subgroup, whereas a peak was observed at 24 hours in the high topical dose subgroup.

In some cases and without wishing to be bound by any particular theory, if vancomycin (topical) levels are detected in the one or more layers of the cutaneous layers and the vancomycin (topical) level is higher than the vancomycin IV level in the same cutaneous layer, it would indicate the penetrability of the vancomycin (topical) and for treatment of cutaneous infections in that the layer(s) of skin. The ratio of the vancomycin (topical) level to the vancomycin IV was higher in the epidermis layer than in the dermis layer, muscle at dose site, or muscle 1 inch away from dose site. A comparison of the dermis and muscle at dose site showed that the ratio of the vancomycin (topical) level to the vancomycin IV was higher in the muscle at dose site than in the dermis layer. The ratios were comparable in both the dermis layer and the muscle at 1 inch away from dose site.

At the epidermis layer, a higher ratio was observed for the high topical dose subgroup than for the low topical dose subgroup. In some cases and without wishing to be bound by any particular theory, this indicates that diseases affecting the epidermis layer would benefit from receiving vancomycin (topical). In some cases and without wishing to be bound by any particular theory, this indicates that diseases affecting the epidermis layer would benefit from receiving a high topical dose of vancomycin.

At the dermis layer, muscle at dose site, and muscle 1 inch away from dose site, higher ratios were observed in the high topical dose subgroups. In some cases and without wishing to be bound by any particular theory, this indicates that diseases affecting the dermis layer, muscle at dose site, and muscle 1 inch away from dose site would benefit from receiving a high topical dose of vancomycin.

Effect of Vancomycin in Animals with Abraded Skin

In animals with abraded skin, a higher amount of vancomycin (topical) was observed in the epidermis layer (FIG. 4), than in the dermis layer (FIG. 5). Low levels were observed in both the muscle at dose site (FIG. 6), and the muscle 1 inch away from dose site (FIG. 7). At the epidermis layer, animals receiving a high topical dose exhibited a higher concentration than animals receiving a low topical dose. In addition, both subgroups, low topical dose and high topical dose, reached a peak concentration at 4 hours. At the dermis layer, a peak concentration was observed at 24 hours in both the low topical dose and high topical dose subgroups. Abraded skin as used herein refers to an injury to the skin at the epidermis level. In some case and without wishing to be bound by any particular theory, the faster reach in peak concentration at the epidermis layer suggested easier penetration, whereas it did not affect the time that it took for vancomycin to penetrate into the dermis layer. In muscle at dose site, a peak was observed at 24 hours in the low topical dose subgroup, but a peak was observed at 4 hours in the high topical dose subgroup.

Similar to the non-abraded group, the ratio of the vancomycin (topical) level to the vancomycin IV was higher in the epidermis layer than in the dermis layer, muscle at dose site, or muscle 1 inch away from dose site. A comparison of the dermis and muscle at dose site showed that the ratio of the vancomycin (topical) level to the vancomycin IV was higher in the muscle at dose site than in the dermis layer. The ratio in the dermis layer in the high dose group was higher in comparison to the muscle at 1 inch away from dose site.

At the epidermis layer, a higher ratio was observed for the high topical dose subgroup than for the low topical dose subgroup. In some cases and without wishing to be bound by any particular theory, this indicates that diseases affecting the epidermis layer would benefit from receiving vancomycin (topical). In some cases and without wishing to be bound by any particular theory, this indicates that diseases affecting the epidermis layer would benefit from receiving a high topical dose of vancomycin.

At the dermis layer, and muscle at dose site, higher ratios were observed in the high topical dose subgroups. At the muscle 1 inch away from dose site, a higher ratio was observed in the low topical dose subgroup. In some cases and without wishing to be bound by any particular theory, these results indicate that diseases affecting the dermis and muscle at dose site would benefit from receiving a high topical dose of vancomycin.

The concentration of vancomycin in the epidermis layer in the abraded skin group was higher than in the nonabraded skin group in the low topical dose subgroup. Furthermore, a higher ratio of the vancomycin (topical) level to the vancomycin IV in the epidermis layer was observed in the abraded skin group at low topical dose subgroup. At the high topical dose subgroup, the concentration and the ratio were higher in the non-abraded skin group.

Additional comparison between the non-abraded skin group vs. the abraded skin group showed that a higher ratio was observed for the high topical dose subgroup in abraded skin group at the dermis layer, and the muscle at dose site. A similar ratio was observed in the low topical dose subgroup in both non-abraded skin group and the abraded skin group in the dermis layer. In some cases and without wishing to be bound by any particular theory, abraded skin lead to a better penetration of vancomycin in both the epidermis and the dermis layers.

Example 7

This experiment tests higher concentrations and repeat doses of topical vancomycin. The experiment is similar in design to Example 6, but animals will receive repeated doses of the topical ointment and vancomycin intravenous.

Additional groups of animals are added that receive both the topical ointment and vancomycin intravenous to determine if the addition of the ointment can enhance the concentration/MIC ratio to a level of 10 times or higher and prolong the time of peak tissue levels without raising the systemic exposure to toxic levels.

Example 8

Clinical trials are performed to investigate the efficacy and safety of topical vancomycin ointment in patients with cutaneous infections caused by susceptible organisms, including methicillin-resistant *Staphylococcus aureus* (MRSA) or methicillin-resistant *Staphylococcus epidermidis* (MRSE). The clinical trials are single center or multicenter randomized studies. Patient selection criteria include (i) cutaneous infection caused by susceptible organisms, including MRSA or MRSE and (ii) nonneutropenic (an absolute neutrophil count of ≥1,000 cells/mm). Topical vancomycin ointment either alone or in combination with a second therapeutic agent is administered at least once daily.

The subjective and objective clinical scores and bacterial cultures are collected at numerous visit days. The primary outcome is the clinical response evaluation (efficacy rate) in which it is determined as complete response, partial response, no response and worsening. Secondary outcome is the eradication of the bacteria. Safety is assessed by adverse events including cases in which neither MRSA nor MRSE is detected.

The examples and embodiments described herein are for illustrative purposes only and various modifications or changes suggested to persons skilled in the art are to be included within the spirit and purview of this application and scope of the appended claims.

What is claimed is:

1. A skin ointment composition for treating a skin condition caused by bacterial infection at a target depth, the composition comprising: multiparticulate vancomycin hydrochloride; and an ointment base selected from the group consisting of liquid paraffin, white petrolatum, purified lanolin, white ointment base, simple ointment base, and mixtures thereof, wherein the composition provides therapeutically effective amount of vancomycin at the target depth of the bacterial infection.

2. The composition of claim 1, wherein the composition comprises about 0.01% to about 10% of vancomycin hydrochloride.

3. The composition of claim 1, wherein the composition provides therapeutically effective amount of vancomycin at the target depth of the bacterial infection selected from an epidermis layer, a dermis layer, a subcutaneous tissue layer, a muscle, or combinations thereof.

4. The composition of claim 3, wherein the composition provides therapeutically effective amount of vancomycin at the target depth at a concentration of at least 10 times higher than the minimum inhibitory concentration (MIC).

5. The composition of claim 1, wherein the topical ointment provides reduced systemic exposure to vancomycin hydrochloride as compared to therapeutically effective doses of IV vancomycin.

6. The composition of claim 1, wherein the multiparticlate vancomycin hydrochloride has an average particle size of from about 1 μm to about 100 μm.

7. A method of treating a skin condition caused by bacterial infection at a target depth, comprising applying to a skin a topical ointment comprising vancomycin hydrochloride as an active ingredient, wherein the topical ointment comprises multiparticulate vancomycin hydrochloride, and an ointment base comprising, liquid paraffin, white petrolatum, purified lanolin, white ointment base, simple ointment base, and mixtures thereof, and wherein the topical ointment provides therapeutically effective amount of vancomycin at the target depth of the bacterial infection.

8. The method of claim 7, wherein the topical ointment comprises about 0.01% to about 10% of vancomycin hydrochloride.

9. The method of claim 7, wherein the topical ointment provides therapeutically effective amount of vancomycin at the target depth of the bacterial infection selected from an epidermis layer, a dermis layer, a subcutaneous tissue layer, a muscle, or combinations thereof.

10. The method of claim 7, wherein the topical ointment provides therapeutically effective amount of vancomycin at the target depth at a concentration of at least 10 times higher than the minimum inhibitory concentration (MIC).

11. The method of claim 7, wherein the topical ointment provides reduced systemic exposure to vancomycin hydrochloride as compared to therapeutically effective doses of IV vancomycin.

12. The method of claim 7, wherein the micronized vancomycin hydrochloride has an average particle size of from about 1 μm to 100 μm.

13. The method of claim 7, wherein the skin condition comprises impetigo, ecthyma, Staphylococcal scalded skin syndrome (SSSS), erysipelas, cellulitis, abscess, necrotizing fasciitis, folliculitis, furunculosis, carbunculosis, secondary skin infection, or a combination thereof.

14. The method of 13, wherein the skin condition is caused by or complicated by Gram positive bacteria selected from *Staphylococcus aureus, Staphylococcus epidermidis*, methicillin-resistant *Staphylococcus aureus* (MRSA), methicillin-resistant *Staphylococcus epidermidis* (MRSE), *Steptococcus pyogenes, Steptococcus agalactiae*, or combination thereof.

\* \* \* \* \*

UNITED STATES PATENT AND TRADEMARK OFFICE
CERTIFICATE OF CORRECTION

PATENT NO. : 9,241,971 B1
APPLICATION NO. : 14/495669
DATED : January 26, 2016
INVENTOR(S) : Barry Butler et al.

Page 1 of 1

It is certified that error appears in the above-identified patent and that said Letters Patent is hereby corrected as shown below:

ON THE TITLE PAGE

Item (72) Inventors:

Change "William Stringer, St. Petersburg, IL" to -- William Stringer, St. Petersburg, FL --

Signed and Sealed this
Nineteenth Day of April, 2016

Michelle K. Lee
*Director of the United States Patent and Trademark Office*